(12) United States Patent
Okawa et al.

(10) Patent No.: US 8,896,680 B2
(45) Date of Patent: Nov. 25, 2014

(54) ENDOSCOPE WITH FIRST AND SECOND VOLTAGE COMPARING PORTIONS

(71) Applicant: Olympus Medical Systems Corp., Tokyo (JP)

(72) Inventors: Fumiyuki Okawa, Tama (JP); Jun Konishi, Hachioji (JP); Hidenori Hashimoto, Sagamihara (JP); Yasuhiro Tanaka, Machida (JP); Yasunori Matsui, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 13/857,435

(22) Filed: Apr. 5, 2013

(65) Prior Publication Data
US 2013/0265403 A1 Oct. 10, 2013

Related U.S. Application Data

(63) Continuation of application No. PCT/JP2012/073787, filed on Sep. 18, 2012.

(30) Foreign Application Priority Data

Sep. 22, 2011 (JP) ................................. 2011-207465

(51) Int. Cl.
| | |
|---|---|
| *A61B 1/06* | (2006.01) |
| *A61B 1/04* | (2006.01) |
| *G02B 23/24* | (2006.01) |
| *A61B 1/00* | (2006.01) |
| *A61B 1/045* | (2006.01) |
| *H04N 5/225* | (2006.01) |

(52) U.S. Cl.
CPC ...... *H04N 5/2253* (2013.01); *H04N 2005/2255* (2013.01); *A61B 1/04* (2013.01); *G02B 23/2469* (2013.01); *A61B 1/00032* (2013.01); *A61B 1/045* (2013.01)
USPC .......................................................... 348/76

(58) Field of Classification Search
USPC .......................................................... 348/76
See application file for complete search history.

(56) References Cited

U.S. PATENT DOCUMENTS

| | | | |
|---|---|---|---|
| 5,402,769 A | 4/1995 | Tsuji | |
| 2008/0027284 A1 | 1/2008 | Suda | |
| 2008/0232131 A1* | 9/2008 | Suda | ............................ 362/574 |

FOREIGN PATENT DOCUMENTS

| | | |
|---|---|---|
| EP | 0 566 861 A1 | 10/1993 |
| JP | 5-168588 A | 7/1993 |

(Continued)

OTHER PUBLICATIONS

Tokumoto, J., "Control Technology and Drive Circuit Designing of CCD", Transistor Technology, Feb. 2005, pp. 139-149 together with an English language translation.

*Primary Examiner* — Dave Czekaj
*Assistant Examiner* — Leron Beck
(74) *Attorney, Agent, or Firm* — Scully, Scott, Murphy & Presser, PC

(57) ABSTRACT

An endoscope includes: an image pickup device mounted in a distal end portion of an insertion portion; wiring that transmits a power supply having a plurality of different power supply voltages for driving the image pickup device, a drive signal that drives the image pickup device, an image pickup signal that is outputted from the image pickup device, and a ground level; a substrate on which a connector that relays the wiring is provided; a first voltage comparing portion that compares the plurality of different power supply voltages; a power supply generation portion that generates a plurality of second power supply voltages; a second voltage comparing portion that compares the plurality of second power supply voltages; and a power supply control portion that controls a supply of power to the image pickup device based on comparison results of the first and second voltage comparing portions.

14 Claims, 22 Drawing Sheets

(56) References Cited

FOREIGN PATENT DOCUMENTS

| | | |
|---|---|---|
| JP | 6-157 A | 1/1994 |
| JP | 7-194530 A | 8/1995 |
| JP | 2005-279125 A | 10/2005 |
| JP | 2008-29557 A | 2/2008 |
| JP | 2008-295589 A | 12/2008 |
| JP | 2008-307293 A | 12/2008 |

* cited by examiner

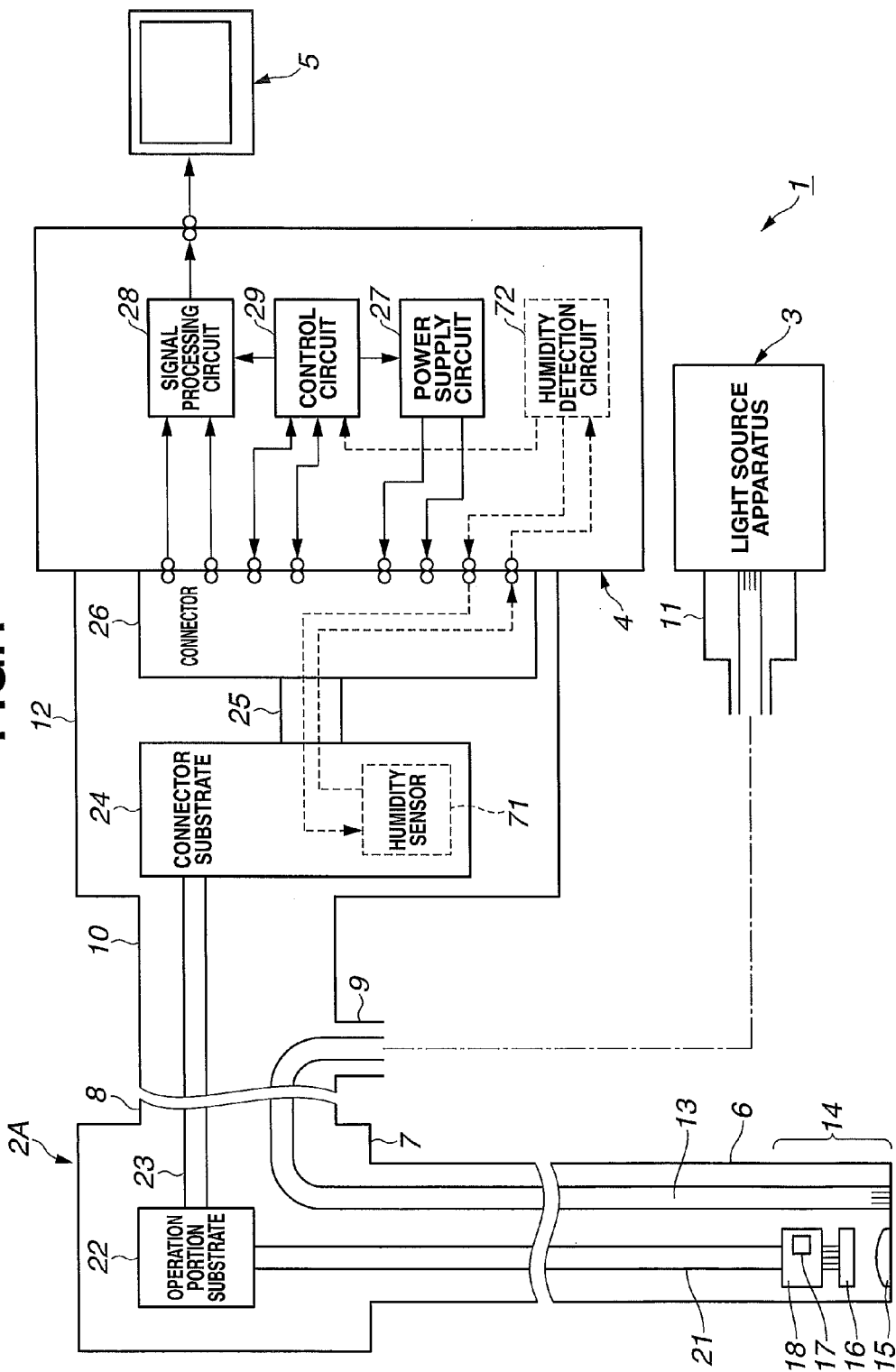

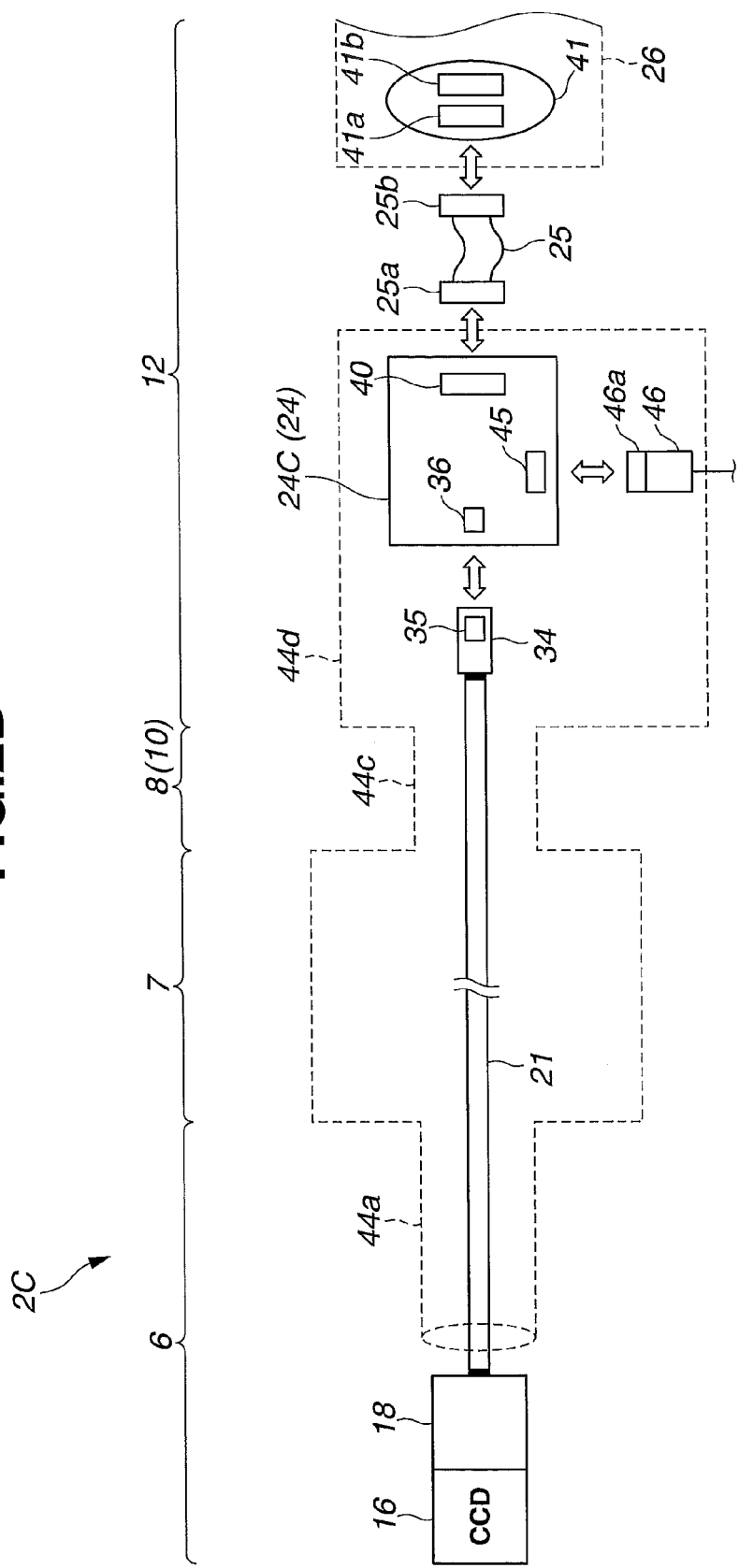

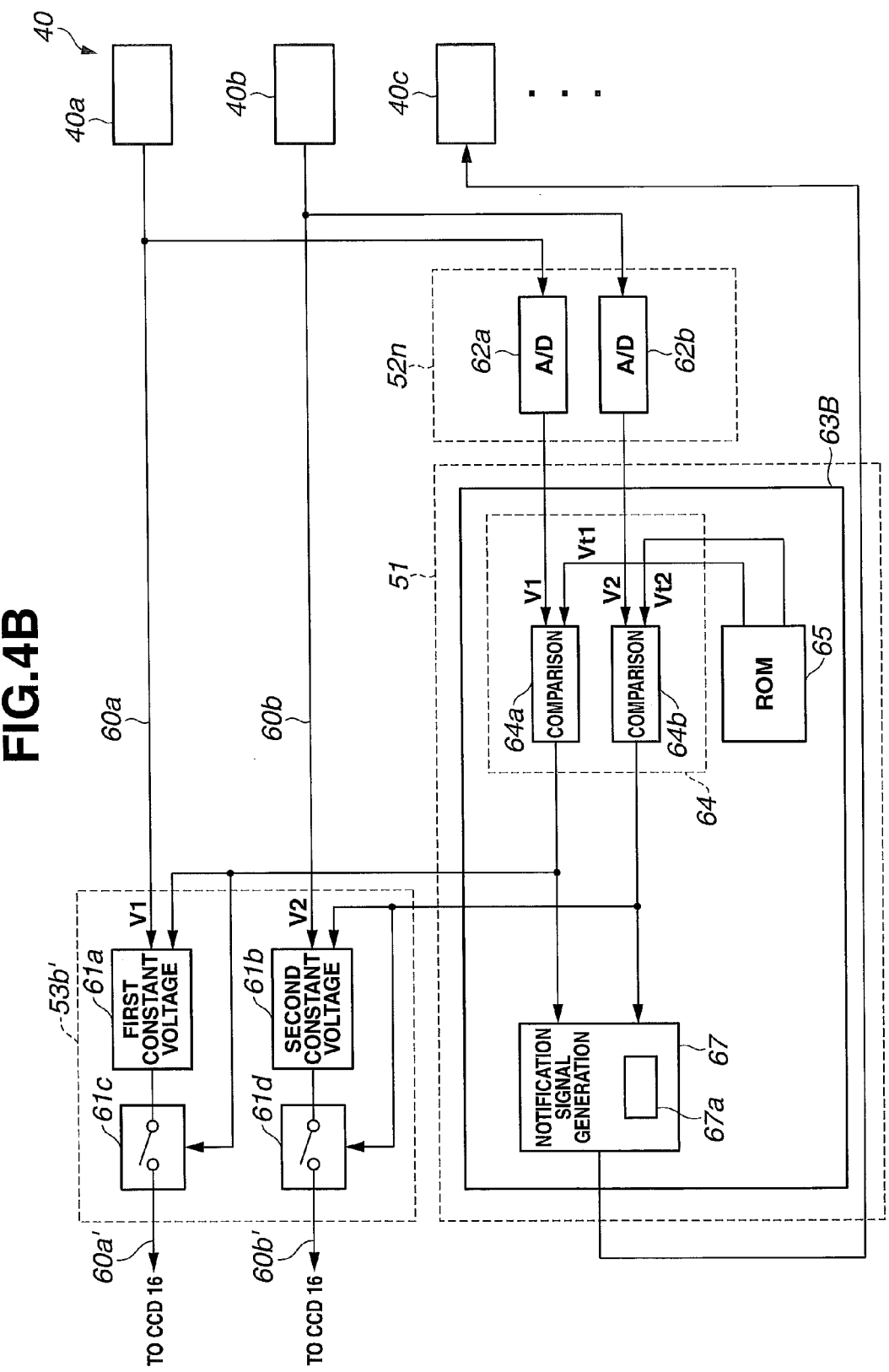

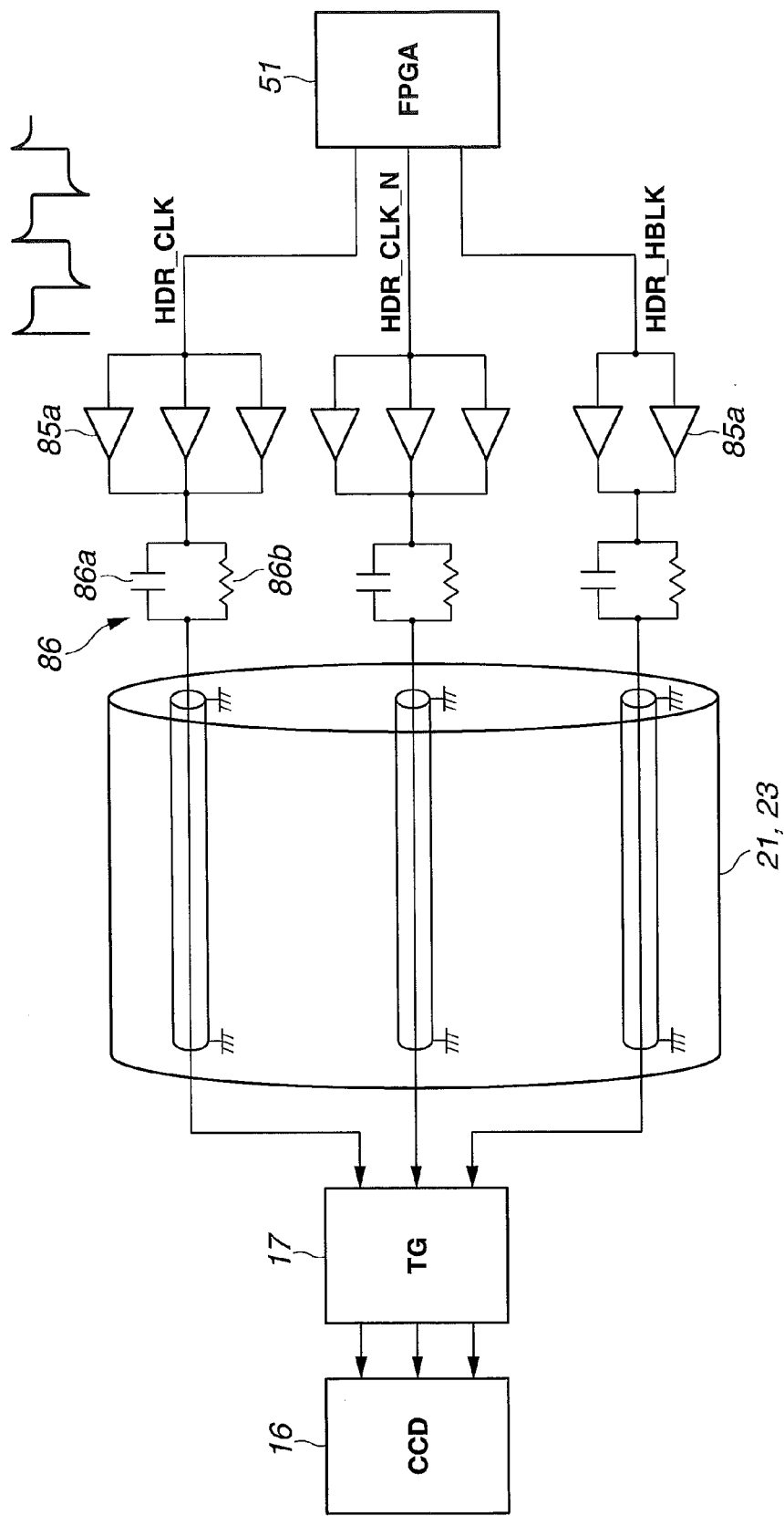

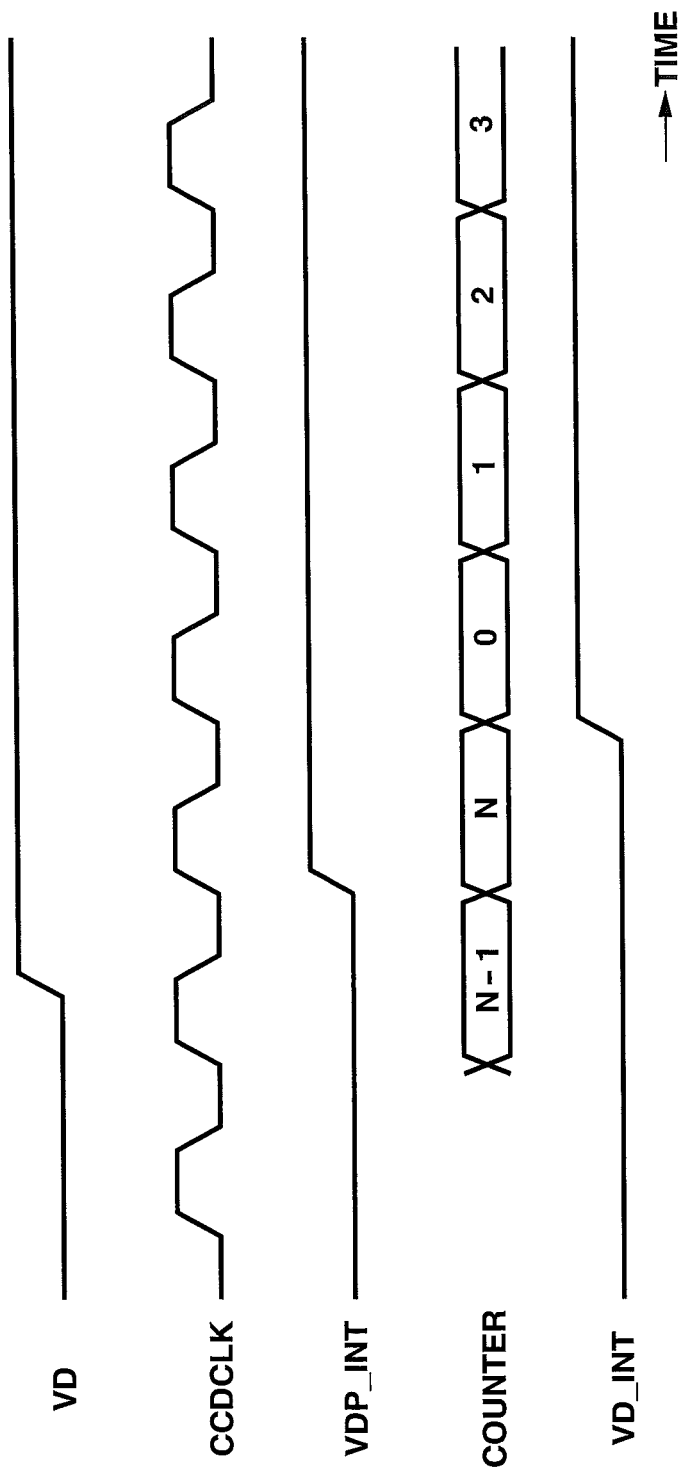

ENDOSCOPE WITH FIRST AND SECOND VOLTAGE COMPARING PORTIONS

CROSS REFERENCE TO RELATED APPLICATION

This application is a continuation application of PCT/JP2012/073787 filed on Sep. 18, 2012 and claims benefit of Japanese Application No. 2011-207465 filed in Japan on Sep. 22, 2011, the entire contents of which are incorporated herein by this reference.

BACKGROUND OF THE INVENTION

1. Field of the Invention

The present invention relates to an endoscope that includes an image pickup device.

2. Description of the Related Art

In recent years, endoscopes in which an image pickup device is provided have been widely used in medical and industrial fields.

To ensure favorable insertability of the endoscope into a body cavity or the like, it is desirable for an endoscope to have an insertion portion with a small diameter.

Further, an endoscope is used in which an image pickup device that is mounted in a distal end portion of the insertion portion is a small size. In order to drive the image pickup device, it is necessary to insert a cable that includes a plurality of signal wires that transmit a plurality of power supplies of different voltages, a drive signal that electrically drives the image pickup device, and an image pickup signal that is outputted from the image pickup device in accordance with application of the drive signal thereto and the like, through the inside of the insertion portion.

Various kinds of endoscopes in which the number of pixels of a solid image pickup device varies according to the purpose of the endoscopy are in practical use, and a load on the side of a processor as a signal processing apparatus that is detachably connected to the endoscope is also increasing.

Therefore, it is desirable to enable the performance of endoscopy using a common processor for which a load has been reduced also in the case of different kinds of endoscopes by, on the side of the respective endoscopes, generating a drive signal that corresponds to the image pickup device mounted in the relevant endoscope and providing a circuit substrate (also referred to as simply "substrate") that performs pre-processing that is suited to the relevant image pickup device with respect to an image pickup signal that is outputted from the image pickup device.

When providing a substrate inside an endoscope, to ensure favorable assemblability and the like, a small-size connector that relays a cable (wiring) is also required, and when a small-size connector is used, a space between adjacent connector contact pins also decreases. Consequently, it is necessary to implement a countermeasure to deal with the occurrence of a short circuit or the like between connector contact pins.

For example, in Japanese Patent Application Laid-Open Publication No. 2008-307293 as a first conventional example, as an image pickup apparatus that includes an image pickup device and a circuit substrate mounted in a distal end portion of an insertion portion, a configuration is adopted in which ground signal wire binding sections are arranged at positions that deviate from each other to facilitate the performance of work to solder a cable to the image pickup apparatus.

Further, in Japanese Patent Application Laid-Open Publication No. 2008-295589 as a second conventional example, an endoscope apparatus is disclosed that detects a variation in a voltage value of a driving power source so as to actuate a voltage detection function even in a standby state.

SUMMARY OF THE INVENTION

An endoscope according to one aspect of the present invention includes: an image pickup device that is mounted in a distal end portion of an insertion portion; wiring that transmits a power supply having a plurality of different power supply voltages for driving the image pickup device, a drive signal that drives the image pickup device, an image pickup signal that is outputted from the image pickup device that is driven by the drive signal, and a ground level; a substrate in which a connector that relays the wiring is provided; a first voltage comparing portion that compares the plurality of different power supply voltages; a power supply generation portion that, based on the plurality of different power supply voltages, generates a plurality of second power supply voltages that are respectively different from the plurality of different power supply voltages; a second voltage comparing portion that compares the plurality of second power supply voltages; and a power supply control portion that controls a supply of power to the image pickup device based on a comparison result of the first voltage comparing portion and a comparison result of the second voltage comparing portion.

BRIEF DESCRIPTION OF THE DRAWINGS

FIG. 1 is a view that illustrates the overall configuration of an endoscope apparatus according to a first embodiment of the present invention;

FIG. 2D is a view that illustrates the configuration of an electric system in an endoscope in which a connector substrate is formed by a single A/D substrate;

FIG. 2E is a circuit diagram that illustrates the circuit configuration of an input protection circuit that protects from static electricity and the like;

FIG. 4B is a view that illustrates the configuration of a CCD power supply voltage monitoring circuit that is a modification of the circuit shown in FIG. 4A;

FIG. 5A is a view that illustrates the configuration of drive means that drives a cable that is connected to a timing generator from an FPGA;

FIG. 5E is a drawing for explaining operations shown in FIG. 5D;

DETAILED DESCRIPTION OF THE PREFERRED EMBODIMENT

An embodiment of the present invention is described hereunder with reference to the drawings.
(First Embodiment)

As shown in FIG. 1, an endoscope apparatus 1 that is equipped with a first embodiment of the present invention includes: an endoscope 2A that includes an image pickup device; a light source apparatus 3 to which the endoscope 2A is detachably connected, and which supplies illuminating light to the endoscope 2A; a processor 4 as a signal processing apparatus that performs signal processing and the like, to which the endoscope 2A is detachably connected; and a monitor 5 as a display apparatus that displays an image signal that is generated by the processor 4 as an endoscopic image.

Figure 2A:
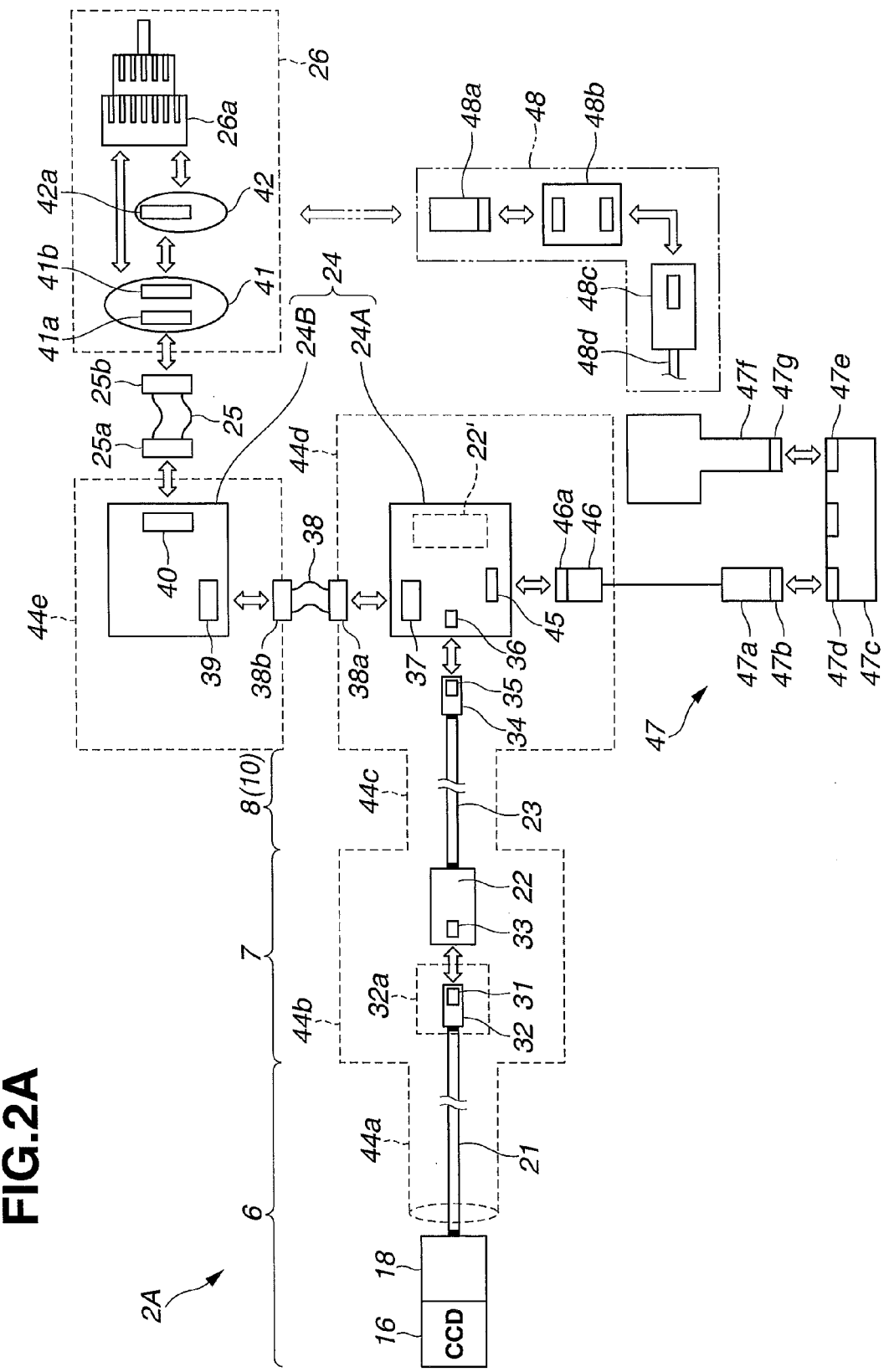
FIG. 2A is a view that illustrates the configuration of an electric system in an endoscope according to the first embodiment.
Figure 2B:
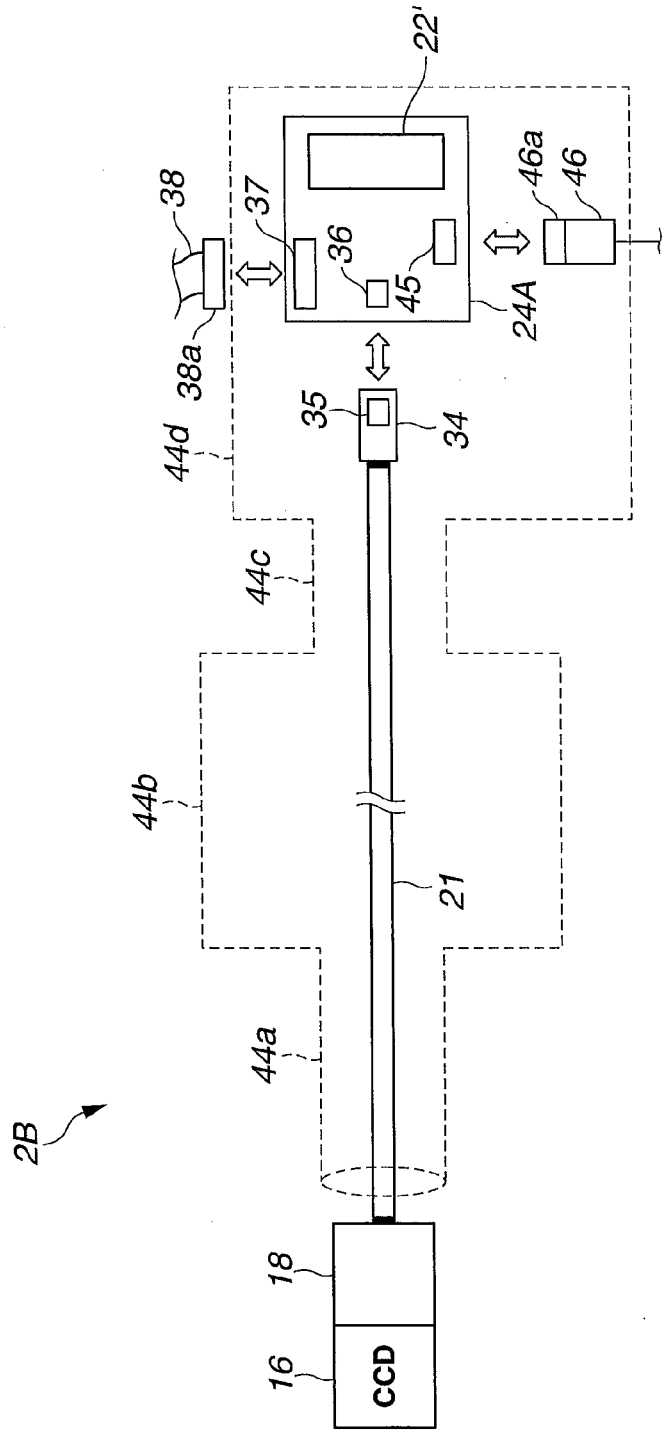
FIG. 2B is a view that illustrates the configuration of an electric system in an endoscope in which one part is different from the endoscope shown in FIG. 2A.

In addition to the endoscope 2A shown in FIG. 1, an endoscope 2B that is shown in FIG. 2B can also be detachably connected to the light source apparatus 3 and the processor 4, and can be used for endoscopy in the same manner as the endoscope 2A. Note that a configuration indicated by a dashed line in FIG. 1 is described later.

The endoscope 2A includes an elongated insertion portion 6 that is inserted into a body cavity, an operation portion 7 provided at a read end of the insertion portion 6, and a universal cord 8 that is extended from the operation portion 7. The universal cord 8 branches into a light guide cord 9 and a signal cord (signal cable) 10 in the vicinity of a proximal end thereof or partway along the universal cord 8. A light source connector 11 at an end portion of the light guide cord 9 is detachably connected to the light source apparatus 3. A signal connector 12 at an end portion of the signal cord 10 is detachably connected to the processor 4 as an external apparatus of the endoscopes 2A and 2B.

A light guide 13 that transmits illuminating light is inserted through the inside of the insertion portion 6, the operation portion 7, and the universal cord 8. By connecting the light source connector 11 to the light source apparatus 3, illuminating light from the light source apparatus 3 is transmitted by the light guide 13, and the transmitted illuminating light is emitted from a light guide distal end face that is mounted in an illuminating window provided in a distal end portion 14 of the insertion portion 6. A configuration may also be adopted in which a connector in which the light source connector 11 and the signal connector 12 are integrated is connected to the light source apparatus 3, and signals of the signal connector 12 are exchanged with the processor 4 by means of a cable that connects the light source apparatus 3 and the processor 4.

An observation window (image pickup window) is provided adjacent to the illuminating window in the distal end portion 14. An objective lens 15 that forms an optical image of an object such as an illuminated diseased part is mounted to the observation window. A charge coupled device (abbreviated as "CCD") 16 as an image pickup device is arranged at an image-formation position of the objective lens 15.

In the present embodiment, a distal end portion substrate 18 that includes a timing generator (abbreviated as "TG") 17 as a drive signal generation circuit that generates a drive signal that drives the CCD 16 is arranged in the vicinity of the CCD 16 in the distal end portion 14.

The distal end portion substrate 18 is connected to an operation portion substrate 22 that is provided inside the operation portion 7 via an integrated coaxial cable 21 that is inserted through the inside of the insertion portion 6. The operation portion substrate 22 is connected to a connector substrate 24 provided inside the signal connector 12 via an integrated coaxial cable 23 that is inserted through the inside of the universal cord 8.

The connector substrate 24 is connected to a connector 26 that is detachably connected to the processor 4 via a thin coaxial cable 25.

Note that the integrated coaxial cables 21 and 23 and the thin coaxial cable 25 constitute wiring that transmits (conveys) a power supply and a drive signal and the like to the CCD 16. The thin coaxial cable 25 is formed by twisting the thin coaxial cable 25 portion in order to assemble the endoscope.

When the cable is twisted, since there is a concern that a LVDS (low voltage differential signaling) pair used in signal transmission will separate and increase radiated noise, a twinax cable is used as the thin coaxial cable 25 to reduce radiated noise. Note that the connector 26 includes two substrates as illustrated in FIG. 2A.

The processor 4 includes a power supply circuit 27 that generates a power supply having a plurality of different power supply voltages required for operations of the image pickup device and the like, a signal processing circuit 28 that performs signal processing with respect to an image pickup signal that is outputted from the image pickup device, and a control circuit 29 that performs control that includes control of the power supply circuit 27 and the signal processing circuit 28.

FIG. 2A illustrates the configuration of the electric system of the endoscope 2A shown in FIG. 1.

The distal end portion substrate 18 is connected by soldering to one end (distal end) of the integrated coaxial cable 21. A micro-connector (abbreviated as "MC") substrate 32 in which an MC 31 as a small-size connector is mounted is connected by soldering to the other end (rear end) of the integrated coaxial cable 21. The MC 31 of the MC substrate 32 is connected to a micro-connector receptacle (abbreviated as "MC receptacle") 33 of the operation portion substrate 22. Note that the distal end portion substrate 18 and the integrated coaxial cable 21 may also be connected by means of an MC and an MC receptacle. The MC substrate 32 is also fixed mechanically to the operation portion substrate 22 by a shielding case 32a that is shown by a dashed line. Note that although the integrated coaxial cable 21 that is connected to the distal end portion substrate 18 is relayed by the operation portion substrate 22 and connected to the integrated coaxial cable 23, and a proximal end of the integrated coaxial cable 23 is connected to the connector substrate 24, an integrated cable GND of the integrated coaxial cables 21 and 23 and a GND of a coaxial cable for each signal that is shielded by the integrated cable GND and arranged on an inner side thereof are separated across an area from the insertion portion 6 to the proximal end of the signal cord 10 in the endoscope 2A.

The operation portion substrate 22 is connected by soldering to one end (distal end) of the integrated coaxial cable 23. An MC substrate 34 is connected by soldering to the other end (rear end) of the integrated coaxial cable 23. An MC 35 as a small-size connector is mounted in the MC substrate 34. The MC 35 is connected to an MC receptacle 36 of an interface substrate (abbreviated as "IF substrate") 24A that is included in the connector substrate 24.

A connector 38a provided at one end of a thin coaxial cable 38 is connected to a connector receptacle 37 provided in the IF substrate 24A. A connector 38b provided at the other end of the thin coaxial cable 38 is connected to a connector receptacle 39 of an A/D substrate 24B on which an analog/digital conversion circuit (abbreviated as "A/D") is mounted. A connector 25a as a small-size connector that is provided at one end of the thin coaxial cable 25 is connected to a connector receptacle 40 as a small-size connector receptacle that is provided on the A/D substrate 24B. A connector 25b at the other end of the thin coaxial cable 25 is connected to a connector receptacle 41a of a circular substrate 41 that has the larger size in the connector 26. The circular substrate 41 is connected to a circular substrate 42 that has the smaller size via a connector 41b and a connector receptacle 42a.

The circular substrates 41 and 42 are connected by soldering to a connector plug 26a. The connector plug 26a is detachably connected to a connector receptacle of the processor 4.

Note that although in FIG. 2A the connector substrate 24 is formed with two substrates, namely, the IF substrate 24A and the A/D substrate 24B, in an endoscope 2C illustrated in FIG. 2D that is described later, the connector substrate 24 is constituted by a single A/D substrate 24C, and the A/D substrate 24C includes the functions of the IF substrate 24A.

Further, as shown in FIG. 2A, when a configuration is adopted in which the connector substrate 24 includes two substrates, namely, the IF substrate 24A and the A/D substrate 24B, a ROM that stores information regarding a cable length, correction information for a cable length, a detection circuit for a cable length and the like may be provided on the IF substrate 24A side, and a ROM that stores information regarding the number of pixels and the kind of the CCD 16 and the like may be provided on the A/D substrate 24B side. Note that in a case where the kinds of the A/D substrate 24B have increased also, a configuration may be adopted in which all information regarding the CCD 16 and the cables is compiled and held on the IF substrate 24A side, to thereby enable a reduction in the kinds of the A/D substrate 24B.

In contrast, in the case of the single A/D substrate 24C that is described later, a configuration may be adopted in which the single A/D substrate 24C is mounted in a state in which information relating to a cable length, correction information of a cable length, a detection circuit for a cable length and the like, and the kinds of CCD and the like is compiled and stored therein.

As shown by a dashed line in FIG. 2A, the integrated coaxial cable 21 is shielded by a shield member 44a that is formed by an exterior member of the insertion portion 6. The shield member 44a is electrically connected to a shield member 44b formed by an exterior member of the operation portion 7. The shield member 44b is electrically connected to a shield member 44c formed by an exterior member of the universal cord 8. The shield member 44c is connected to a shield member of the signal connector 12.

Note that in FIG. 2A, as the shield members of the signal connector 12, the IF substrate 24A and the A/D substrate 24B are shielded by shield members 44d and 44e, respectively.

These shield members are brought into conduction (omitted from the drawings) with a ground at one point or a plurality of points on the IF substrate 24A or the A/D substrate 24B inside the signal connector 12.

Further, a connector 46a of a switch flexible substrate 46 that is constituted by a flexible substrate is connected to a connector receptacle 45 provided on the IF substrate 24A. One end of a switch cable is soldered to the switch flexible substrate 46, and the other end of the switch cable is connected by soldering to a flexible substrate 47a that is included in a scope switch 47 that is attached to the operation portion 7.

A connector 47b of the flexible substrate 47a is connected to a connector receptacle 47d of a switch-box flexible substrate 47c. A connector 47g of a switch-relay flexible substrate 47f that relays a switch is further connected to a connector receptacle 47e of the switch-box flexible substrate 47c. Further, with respect to the endoscope 2A, some endoscopes include an insertion shape detection unit (abbreviated as "UPD unit") 48 that detects an endoscope insertion shape.

In this case, as shown by a chain double-dashed line in FIG. 2A, a UPD flexible substrate 48a of the UPD unit 48 is connected to the circular substrate 42 of the signal connector 12, and the UPD flexible substrate 48a is connected to a UPD substrate 48c via a UPD relay substrate 48b that performs a relay function. The UPD substrate 48c is connected to a UPD probe unit 48d that is arranged inside the insertion portion 6.

With respect to the endoscope 2A, endoscopes are also available that include an unshown focal point switching unit that switches a focal point of the objective lens 15. In this case, a drive substrate that drives an actuator that switches a focal point of the objective lens 15 is connected to the circular substrate 41.

Note that the MC substrates 32 and 34, the operation portion substrate 22, the IF substrate 24A, the A/D substrate 24B, the circular substrates 41 and 42, the UPD relay substrate 48b, and the UPD substrate 48c are rigid substrates, while the flexible substrate 47a, the switch-box flexible substrate 47c, and the switch-relay flexible substrate 47f are constituted by a flexible substrate.

FIG. 2B shows the configuration of an endoscope in which, relative to above described endoscope 2A, the operation portion substrate 22 is not provided in the operation portion 7.

In this endoscope 2B, since the operation portion substrate 22 is not provided in the operation portion 7, the MC 34 in the signal connector 12 is connected to the other end of the integrated coaxial cable 21.

Further, to achieve commonality of components with the endoscope 2A, a function of an operation portion substrate 22' that is equivalent to the operation portion substrate 22 is mounted on the IF substrate 24A. In the endoscope 2B, a configuration is adopted whereby, by placing the operation portion substrate 22' of the IF substrate 24A in an operating state or an active state (indicated by a solid line in FIG. 2B), the A/D substrate 24B can correspond to both the endoscope 2A and the endoscope 2B by also performing the same processing as that performed for the endoscope 2A in the case of the endoscope 2B in which the operation portion substrate 22 is not provided in the operation portion 7.

With respect to the IF substrate 24A mounted in the endoscope 2A, the function of the operation portion substrate 22' in the IF substrate 24A is disabled (indicated by a dashed line in FIG. 2A). Since the remaining configuration of the endoscope 2B is the same as that of the endoscope 2A, illustration of the A/D substrate 24B and the like is omitted from the drawings. Note that the IF substrate 24A and the A/D substrate 24B are separated in front of an LPF 52i that is described later.

Figure 2C:
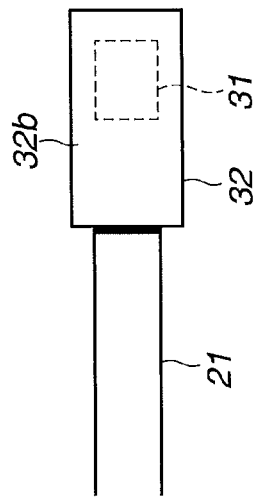
FIG. 2C is a view that illustrates a back surface of a microconnector substrate shown in FIG. 2A.

Note that, the back surface (when a face on which the MC 31 is provided is taken as the front surface) of the MC substrate 32 in FIG. 2A is shown in FIG. 2C. An all-ground face 32b in which the entire face is a metal face is formed on the back surface of the MC substrate 32. Further, as well as connection with a ground (potential) by connection between the MC 31 and the MC receptacle 33, electrical connection with a ground can also be made by means of the shielding case 32a that contacts the all-ground face 32b, so that unwanted noise emission and the like can be reduced. Note that in a case where the electrical conductivity of the above described shield member is favorable, a configuration may be adopted in which a pattern is made that forms the all-ground face 32b in which the entire face is a metal face, and in a case where electrical connection with the all-ground face 32b varies at portions at which electrical conductivity of the shield member is poor, a configuration may be adopted in which the all-ground face 32b is eliminated. Further, with respect to the all-ground face 32b, if a metal face is provided at which a mechanical contact point with the shield member can be made, a configuration may be adopted in which a ground face is provided at one part thereof, and the all-ground face 32b is not provided over the entire face.

According to the present embodiment, in addition to the endoscopes 2A and 2B shown in FIG. 2A and FIG. 2B, as shown in FIG. 2D, a configuration of an endoscope 2C in which the connector substrate 24 is formed by only the A/D substrate 24C (and does not include two substrates, i.e. the IF substrate 24A and the A/D substrate 24B) may be adopted. In the configuration of the endoscope 2C, the operation portion substrate 22 is not provided in the operation portion 7, similarly to the case shown in FIG. 2B.

Since the remaining configuration is mostly the same as that of the endoscope 2B shown in FIG. 2B, the same constituent elements are denoted by the same reference symbols, and a description thereof is omitted. The endoscope 2C can also be detachably connected to the processor 4. When the endoscope 2C is connected thereto, the processor 4 performs processing that corresponds to the image pickup device and the like mounted in the endoscope 2C, similarly to a case in which the endoscope 2A or 2B is connected.

Figure 2E:
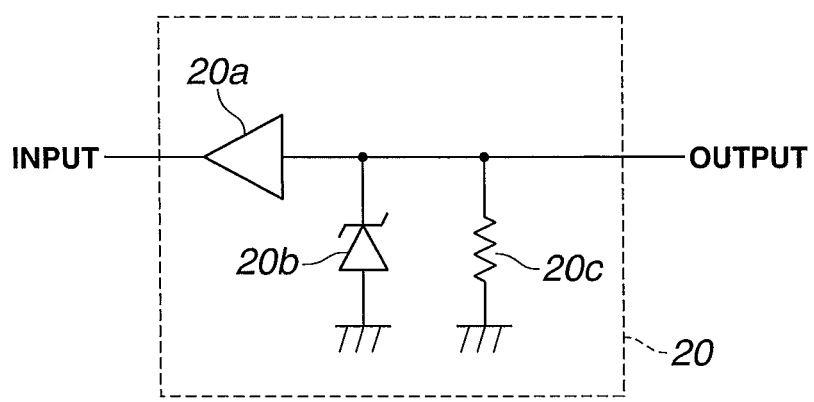

Note that in the connector 26, for example, as shown in FIG. 2E, in the circular substrate 41, an input protection circuit 20 is provided that protects circuits inside the endoscope 2A from an excessive voltage such as static electricity. A signal that is inputted to the endoscope 2A via the connector plug 26a from the processor 4 side is outputted to the connector substrate 24 side via a buffer 20a.

An input terminal of the buffer 20a is protected by a Zener diode (voltage regulator diode) 20b that makes an excessive voltage a predetermined voltage and a resistance 20c that pulls down the voltage. That is, at the input terminal of the buffer 20a, an anode thereof is grounded by the Zener diode 20b to which a cathode is connected, and the input terminal is also grounded via the resistance 20c.

In a case where an excessive voltage such as static electricity is inputted to the connector plug 26a, the excessive voltage is caused to undergo a voltage drop to a Zener voltage that is a predetermined voltage that is allowed by the Zener diode 20b and is also discharged to the ground side by the resistance 20c, to thereby swiftly reduce the excessive voltage. Note that the Zener voltage of the Zener diode 20b is set to a permitted predetermined voltage (for example, about 10 V) that is allowed, and the resistance 20c is set to a resistance value that is a small load with respect to a signal that is actually inputted.

Although one input protection circuit 20 is shown in FIG. 2E, a configuration may be adopted in which similar input protection circuits 20 are provided for a plurality of signals that are inputted to the connector substrate 24 side via the connector plug 26a.

Note that in the case of outputting a signal to the processor 4 side via the connector plug 26a from the endoscope 2A, a configuration may also be adopted in which the Zener diode and the resistance 20c are provided at an output terminal of a buffer that outputs the signal so as to protect the output terminal of the buffer from an excessive voltage such as static electricity.

Figure 3:
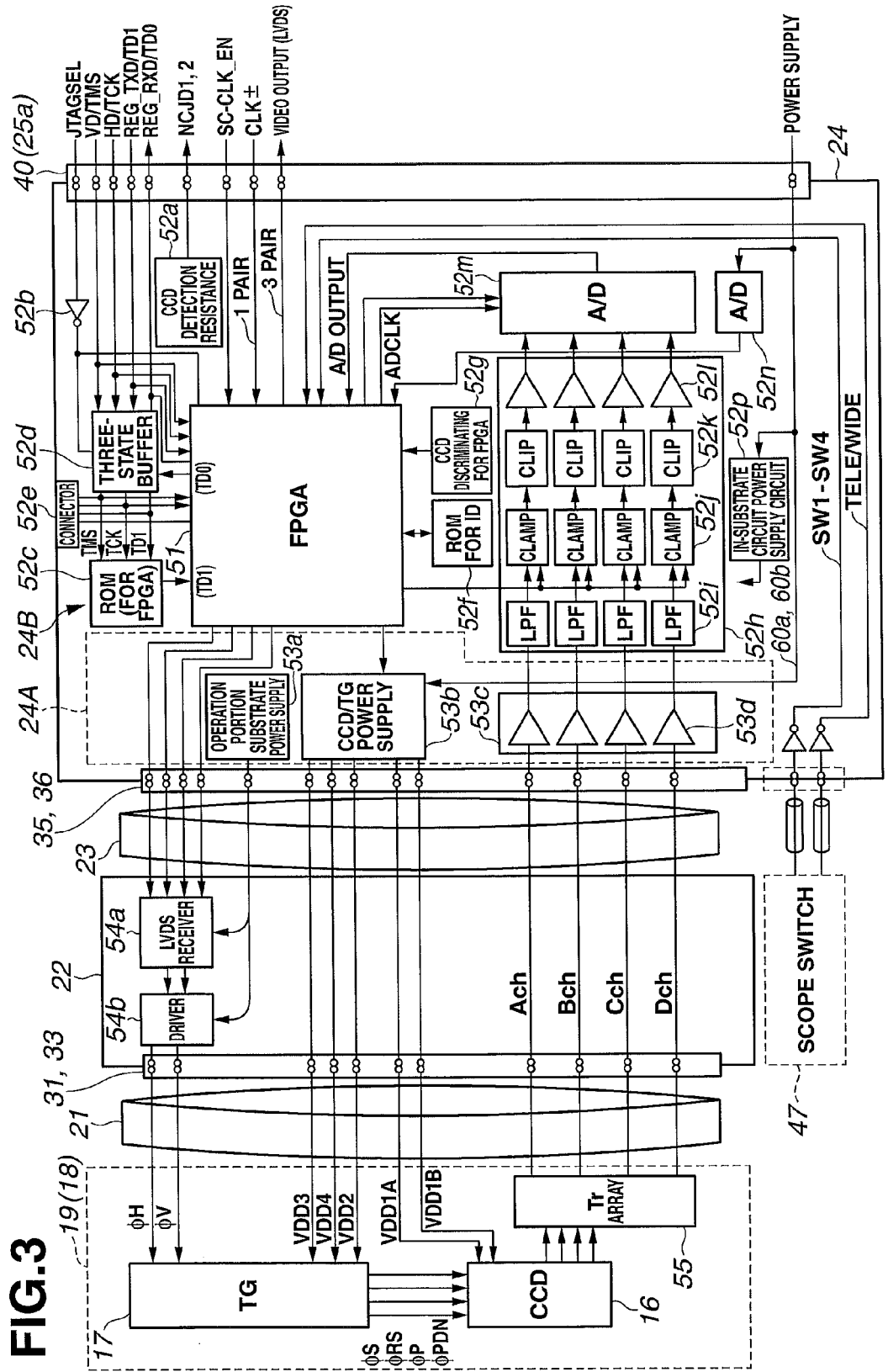
FIG. 3 is a view that illustrates a specific configuration of the electric system shown in FIG. 2A.

FIG. 3 shows the detailed configuration of the electric system in the endoscope 2A. A field-programmable gate array (abbreviated as "FPGA") 51 as a programmable LSI (large scale integrated circuit) is provided inside the A/D substrate 24B. The FPGA 51 is responsible for transmission control of synchronizing signals for driving the CCD 16, transmission processing with respect to various timing signals, processing that converts from an image pickup signal outputted from the CCD 16 into a signal form for performing high-speed signal transmission, and processing for a power supply voltage and the like.

Further, the FPGA 51 performs transmission and reception of JTAGSEL, VD/TMS, HD/TCK, REG_TXD/TDO, REG_RXD/TDI, NCJD1,2, SC_CLK_EN, CLK±, and video output (LVDS) signals with (the signal processing circuit 28 and the control circuit 29 of) the processor 4 side via the connector 25a.

Power supply of a plurality of power supply voltages from the power supply circuit 27 of the processor 4 is supplied to the A/D substrate 24B.

JTAGSEL is a signal that is utilized when rewriting data of the FPGA 51 that is stored in a ROM 52c from the processor 4 side utilizing a JTAG (Joint Test Action Group) standard.

VD and HD represent a vertical synchronizing signal and a horizontal synchronizing signal, respectively. VD and HD are selectively used with TMS (test mode select) and TCK (test clock), respectively.

REG_TXD represents a signal used when transmitting transmission data from the FPGA 51 to the processor 4 side, and REG_TXD is selectively used with a TDO (test data out) signal.

REG_RXD represents a signal used when the FPGA 51 receives reception data from the processor 4 side, and is selectively used with a TDI (test data in) signal.

NCJD1,2 represents a signal from a CCD detection resistance 52a that detects the kind of the CCD 16 that is mounted in each endoscope 2A.

SC_CLK_EN is a pulsed signal that is notified in advance (immediately before) to the FPGA 51 on the endoscope 2A side when starting the power supply and clock from the processor 4. When the power supply of the processor 4 is turned off, a signal indicating that the power supply is being turned off is also notified in advance to the FPGA 51 so that predetermined shutdown processing can be executed on the endoscope 2A side (described later referring to FIG. 5B).

CLK± represents a clock that is supplied to the FPGA 51 from the processor 4. The FPGA 51 performs operations that are synchronized with the CLK±. LVDS that is a comparatively high-speed differential interface with a small amplitude and low power consumption is adopted for the CLK±.

The video output is outputted using the LVDS technology from the FPGA 51 to the processor 4 side.

The JTAGSEL signal is inputted to the FPGA 51 via an inverter 52b, and also controls opening and closing of a three-state buffer 52d provided on a signal wire that is connected to the ROM 52c as a memory for writing FPGA data.

The respective signals of VD/TMS, HD/TCK, and REG_RXD/TDI are inputted to the input terminal of the FPGA 51, and are also inputted to the input terminal of the ROM 52c via the three-state buffer 52d. The VD/TMS and HD/TCK signals are also inputted to the input terminal of the FPGA 51.

An output terminal of the FPGA 51 is connected to a signal wire of REG_TXD/TDO via the three-state buffer 52d, and the output terminal of the FPGA 51 is also connected to the signal wire.

An input/output terminal of the ROM 52c is connected to the connector 52e without being connected via the three-state buffer 52d. Writing of FPGA data as program data that determines an LSI that is programmably constructed by the FPGA 51 to the ROM 52c can be performed from the connector 52e. Further, the input/output terminal of the ROM 52c is connected to the FPGA 51.

A ROM for ID 52f in which information (for example, model names) relating to each unique identification (ID) of the respective endoscopes 2A is stored is connected to the FPGA 51.

A CCD discriminating circuit for FPGA 52g that determines the kind of the CCD 16 and the like with respect to the FPGA is connected to the FPGA 51. The CCD discriminating circuit for FPGA 52g, for example, is constituted by a resistance having a resistance value that allows the kind of the CCD 16 to be discriminated.

The FPGA 51 transmits, for example, four signals that are necessary to generate a drive signal that drives the CCD 16 to an LVDS receiver 54a provided inside the operation portion substrate 22.

The LVDS receiver 54a drives a driver 54b, and the driver 54b transmits a generated horizontal transfer signal φH and vertical transfer signal φV to the TG 17 of the distal end portion substrate 18. The TG 17 applies a CCD drive signal that includes four signals (for example, φS, φRS, φP, and φPDN) to the CCD 16, and drives so as to cause a signal charge that has been subjected to photoelectric conversion by the CCD 16 to be outputted as an image pickup signal. In a case where the LVDS receiver 54a and the driver 54b are also arranged on the IF substrate 24A and a drive signal is generated using the operation portion substrate 22, the circuit of the LVDS receiver 54a and the driver 54b arranged on the IF substrate 24A side is bypassed. In contrast, when the operation portion substrate 22 is not used, it is possible to reduce the kinds of substrates prior to mounting of the IF substrate 24A by using the above described circuit that is arranged on the IF substrate 24A side.

Note that, in FIG. 3, SIP 19 that includes the CCD 16 and the distal end portion substrate 18 is shown.

The IF substrate 24A includes an operation portion substrate power supply circuit 53a that supplies power to the operation portion substrate 22. The operation portion substrate power supply circuit 53a supplies power that is necessary for operation of the LVDS receiver 54a and the driver 54b.

The IF substrate 24A also includes a CCD/TG power supply circuit 53b as power supply generation means that is provided inside the endoscope 2A. The CCD/TG power supply circuit 53b supplies a plurality of power supply voltages to the CCD 16 and the TG 17. In the example shown in FIG. 3, the CCD/TG power supply circuit 53b supplies power supplies VDD1A and VDD1B of different power supply voltages via power supply wires 60a' and 60b' to the CCD 16, and supplies VDD2 to VDD4 to the TG 17.

In the present embodiment the CCD 16 has an output function that outputs signals of four channels. Image pickup signals of four channels that are outputted from the CCD 16 are outputted as low-impedance image pickup signals of four channels (abbreviated as "Ach", "Bch", "Cch", and "Dch" in FIG. 3) from a transistor array (abbreviated as "Tr array" in FIG. 3) 55 that includes four transistors.

Note that a configuration may also be adopted that, instead of directly outputting the output signals of the CCD 16 to the transistor array 55, outputs the output signals of the CCD 16 to the transistor array 55 via a correlated double sampling circuit.

The image pickup signals of four channels are inputted to a first analog circuit 53c in the IF substrate 24A. The first analog circuit 53c includes four amplifiers 53d that amplify the inputted image pickup signals, respectively.

Each of image pickup signals that were amplified by the amplifiers 53d is inputted to a second analog circuit 52h in the A/D substrate 24B. The second analog circuit 52h also includes a circuit for four channels to correspond to the image pickups signals of four channels. For example, an image pickup signal of Dch becomes an output signal of the second analog circuit 52h after passing through the LPF 52i, a clamping circuit 52j that performs clamping on the basis of a black level, a clipping circuit 52k that clips an unnecessary level, and an amplifier 52l. A similar configuration is adopted for the other channels also.

The output signals of the second analog circuit 52h are inputted to a four-channel A/D conversion circuit portion (abbreviated as simply "A/D" in FIG. 3) 52m, and are converted to a digital image pickup signal. Note that an A/D conversion clock ADCLK for performing A/D conversion is applied to the A/D conversion circuit portion 52m from the FPGA 51, and the A/D conversion circuit portion 52*m* performs A/D conversion in synchrony with the clock ADCLK.

The A/D conversion circuit portion 52*m* makes A/D-converted output signals of four channels that have undergone A/D conversion into six pairs of A/D-converted output signals (video channel, clock, frame), and outputs the signals to the FPGA 51. The FPGA 51 converts the signals from signals of four channels into signals of three channels, and outputs a video signal using the LVDS scheme of three channels to the processor 4 side. In the LVDS scheme also, it is desirable to take EMI into consideration. The specific details are as follows. When driving the CCD 16 that is mounted in the endoscope 2A, a timing in a horizontal direction and a timing in a vertical direction are taken into consideration, similarly to the scheme for a video signal. At this time, a period in which the CCD 16 is driven in the horizontal direction and a signal from the CCD 16 is extracted, and a period in which the CCD 16 is not driven and a signal is also not extracted exists. If the latter is taken as "H blanking", in order to take EMI into consideration in the H blanking, it is favorable to divide a drive clock signal (for example, 30 MHz) to generate divided clock signals (15 MHz that is half of 30 MHz) and cause the divided clock signal to overlap in the H blanking. In this case, radiated noise is suppressed in the course of transmitting by LVDS. It is also favorable to cause divided clock signals to overlap in a similar manner in V blanking in the vertical direction. Further, a power supply that is supplied at a plurality of power supply voltages (including V1 and V2 shown in FIG. 4A) from the power supply circuit 27 is supplied to (a CCD power supply circuit 53*b*' inside) the CCD/TG power supply circuit 53*b* in the IF substrate 24A via the power supply wires (including 60*a* and 60*b*), and after being converted to a digital voltage by an A/D conversion circuit portion 52*n* in the A/D substrate 24B, is outputted to (a CCD power supply voltage monitoring circuit 63 shown in FIG. 4A that is constructed by) the FPGA 51.

In addition, as shown in FIG. 3, at the connector substrate 24, for example, inside the A/D substrate 24B, an in-substrate circuit power supply circuit 52*p* is provided that generates a power supply voltage necessary for operations of circuits (specifically, the first analog circuit 53*c* and the second analog circuit 53*h* and the like) in the connector substrate 24. As power supply voltages from the power supply wires 60*a* and 60*b* connected to the power supply circuit 27 of the processor 4, the in-substrate circuit power supply circuit 52*p* generates +5V_AFE1, −5V_AFE1, +5V_AFE2, and −5V_AFE2 and the like that are described later.

Further, a signal of the scope switch 47 of the operation portion 7 is inputted to the FPGA 51 via a coaxial cable inside the universal cord and a waveform shaping buffer inside the signal connector 12. For example, on/off signals of four switches SW1 to SW4 provided in the scope switch 47 and operation signals for a telescopic angle (TELE) and a wide angle (WIDE) in a case where an actuator is mounted are inputted into the FPGA 51. The information of these switches undergoes parallel-serial conversion at the FPGA 51 and is transmitted to the processor 4 through a control signal line.

Figure 4A:
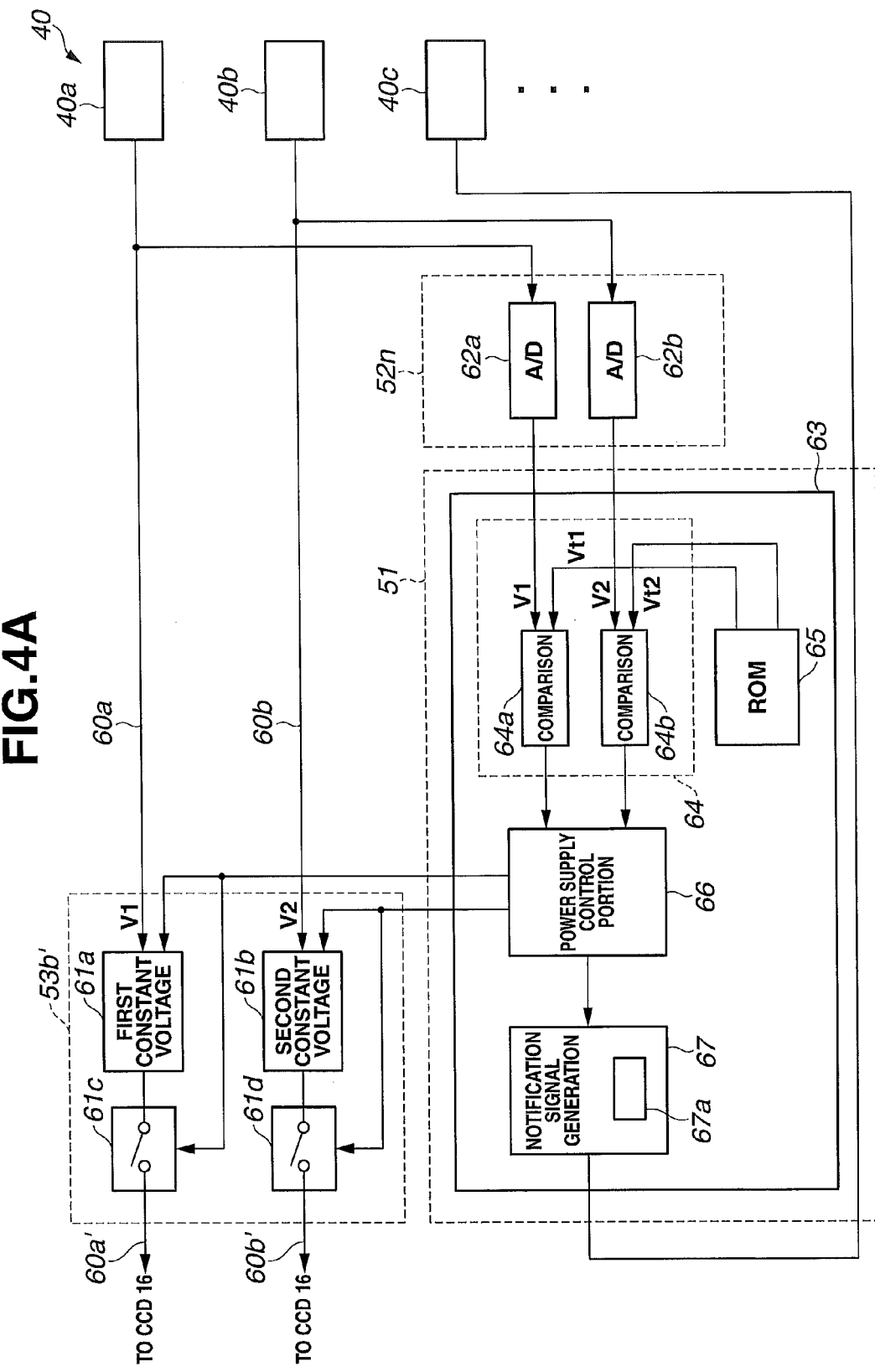
FIG. 4A is a view that illustrates the configuration of a CCD power supply voltage monitoring circuit.

FIG. 4A shows the configuration of the CCD power supply voltage monitoring circuit 63 that is provided inside the connector substrate 24 of the endoscope 2A, and monitors a power supply voltage when power is supplied to the CCD 16 side. Note that a configuration may also be adopted in which the power supply voltage when power is supplied to the TG 17 side is also monitored as well as power that is supplied to the CCD 16 side, such as in the case of the CCD/TG power supply circuit 53*b* shown in FIG. 3.

The thin coaxial connector receptacle 40 has connector-receptacle contact pins 40*a*, 40*b*, and 40*c*, . . . that are electrically connected with connector contact pins of the small-size connector 25*a* by coming in contacting therewith, respectively. Note that, via the thin coaxial cable 25 on which the connector 25*a* is provided and the like, the connector-receptacle contact pins 40*a* and 40*b* and the connector-receptacle contact pin 40*c* are connected with a power supply output terminal of the power supply circuit 27 of the processor 4 and the control circuit 29 of the processor 4, respectively. Accordingly, a power supply of power supply voltages (may sometimes be abbreviated as "voltage") V1 and V2 is supplied from the power supply circuit 27 on the processor 4 side to the connector-receptacle contact pins 40*a* and 40*b*.

The connector-receptacle contact pin 40*a* is connected to an input terminal of a first constant voltage circuit 61*a* forming the CCD power supply circuit 53*b*' (as power supply generation means that generates a plurality of constant power supply voltages (abbreviated as "constant voltage") that are different from the plurality of different power supply voltages V1 and V2 that are inputted) via the power supply wire 60*a*. The connector-receptacle contact pin 40*b* is connected to an input terminal of a second constant voltage circuit 61*b* forming the CCD power supply circuit 53*b*' via the power supply wire 60*b*.

The first constant voltage circuit 61*a* and the second constant voltage circuit 61*b* are converted to predetermined constant voltages (VDD1A and VDD1B in FIG. 3) that are different from each other from the power supply voltages V1 and V2 that are inputted to the input terminals, and are respectively outputted to a power supply terminal of the CCD 16 via the power supply wires 60*a*' and 60*b*'. Note that the power supply wires 60*a*' and 60*b*' are relayed at MCs 31 and 35 and the like as small-size connectors on the way to arriving at the power supply terminal of the CCD 16.

Further, the power supply voltages of the power supply wires 60*a* and 60*b* are converted to digital voltages by A/D conversion circuits 62*a* and 62*b* constituting the A/D conversion circuit portion 52*n*, and thereafter are inputted to the CCD power supply voltage monitoring circuit 63 inside the FPGA 51 (more specifically, constructed by a part of the FPGA 51).

The CCD power supply voltage monitoring circuit 63 includes: comparison circuits 64*a* and 64*b* that compare the digital voltages V1 and V2 generated by the A/D conversion circuits 62*a* and 62*b*, respectively, with threshold values Vt1 and Vt2; a ROM 65 as a memory in which threshold values are stored that outputs the threshold values Vt1 and Vt2 to the comparison circuits 64*a* and 64*b*, respectively; and a power supply control portion 66 that, by comparison results of the comparison circuits 64*a* and 64*b* being inputted thereto, controls the operations for supplying power by the CCD power supply circuit 53*b*'.

In addition, the CCD power supply voltage monitoring circuit 63 includes a notification signal generation circuit 67 that, in a case where the power supply control portion 66 outputs an abnormality judgment signal to the effect that a voltage is abnormal, generates a notification signal for notifying the abnormality. Note that a configuration may also be adopted in which the notification signal generation circuit 67 is provided inside the power supply control portion 66.

The ROM 65 as storage means for threshold values stores threshold values Vt1*a* and Vt2*a* that are somewhat smaller than the voltages V1 and V2 in a normal state, and also stores threshold values Vt1*b* and Vt2*b* that are somewhat larger than the voltages V1 and V2. The ROM 65 outputs the two threshold values Vt1*a* and Vt1*b* as the threshold value Vt1 to the comparison circuit 64*a*, and outputs the two threshold values Vt2*a* and Vt2*b* as the threshold value Vt2 to the comparison circuit 64*b*.

The comparison circuits 64*a* and 64*b* are window-type comparison circuits, respectively, and compare whether or not the voltage V1 is larger than the threshold value Vt1*a*, and whether or not the voltage V1 is smaller than the threshold value Vt1*b*, and output the comparison results to the power supply control portion 66. Note that in FIG. 4A the comparison circuits 64*a* and 64*b* are indicated with a comparison circuit 64.

When the voltage V1 satisfies a condition V1*a*≤V1≤Vt1*b*, the power supply control portion 66 judges that the voltage V1 is a voltage within a normal range. Likewise, when the voltage V2 satisfies a condition V2*a*≤V2≤Vt2*b*, the power supply control portion 66 judges that the voltage V2 is a voltage within a normal range.

In contrast, if the voltage V1 does not satisfy the condition V1*a*≤V1≤Vt1*b*, the power supply control portion 66 judges that the state is an abnormal voltage state in which the voltage V1 is not normal. Likewise, if the voltage V2 does not satisfy the condition V2*a*≤V2≤Vt2*b*, the power supply control portion 66 judges that the state is an abnormal voltage state in which the voltage V2 is not normal.

When the power supply control portion 66 judges that the voltage V1 is an abnormal voltage, the power supply control portion 66 controls so as to stop operations (that generate a power supply of a constant voltage) of the first constant voltage circuit 61*a*, and also controls so as to turn a switch 61*c* off so as to cut off the constant voltage that is supplied to the CCD 16 from the first constant voltage circuit 61*a*.

Further, when the power supply control portion 66 judges that the voltage V2 is an abnormal voltage, the power supply control portion 66 controls so as to stop operations of the second constant voltage circuit 61*b*, and also controls so as to turn a switch 61*d* off so as to cut off the constant voltage that is supplied to the CCD 16 from the second constant voltage circuit 61*b*.

A configuration may also be adopted in which the switch 61*c* provided in the output terminal of the first constant voltage circuit 61*a* is provided inside the first constant voltage circuit 61*a*, and which turns that switch off. A similar configuration can also be applied with respect to the switch 61*d* provided in the output terminal of the second constant voltage circuit 61*b*.

Note that if the power supply control portion 66 judges that both of the voltages V1 and V2 are normal, the power supply control portion 66 causes the CCD power supply circuit 53*b* to continue the operations thereof.

Further, when an abnormality judgment signal is inputted thereto in a case where the power supply control portion 66 judged that the voltage V1 or V2 is an abnormal voltage, the notification signal generation circuit 67 generates a notification signal that notifies to the effect that the voltage V1 or V2 is an abnormal voltage.

The notification signal generation circuit 67 includes notification signal transmission means that, when transmitting the notification signal to the processor 4 side, does not transmit the notification signal using a dedicated signal wire for transmission of the notification signal, but instead superimposes the notification signal upon another signal at a predetermined timing and transmits the notification signal to the processor 4 side by means of a signal wire that transmits the other signal. For example, the notification signal transmission means superimposes (inserts) the notification signal upon (in) the REG-TXD/TDO signal or the vertical synchronizing signal VD shown in FIG. 3 and transmits the signal. Therefore, the notification signal generation circuit 67 includes a notification signal superimposing circuit 67*a* that superimposes the notification signal upon an original control signal or the like. The notification signal, for example, is transmitted to the control circuit 29 side of the processor 4 via the connector contact pin 40*c*.

It is thereby possible to eliminate the need to provide a dedicated signal wire for transmission of the notification signal that is rarely used.

Upon receiving the notification signal that was superimposed upon a control signal or the like, the control circuit 29 outputs the notification signal to the signal processing circuit 28. The signal processing circuit 28 superimposes the notification signal upon a video signal. Subsequently, the monitor 5 displays the notification signal together with an endoscopic image.

The endoscope 2A configured in this manner is characterized by including: the CCD 16 as an image pickup device mounted in the distal end portion 14 of the insertion portion 6; the integrated coaxial cables 21 and 23 as wiring that transmits a power supply having a plurality of different power supply voltages for driving the image pickup device, a drive signal that drives the image pickup device, an image pickup signal that is outputted from the image pickup device that is driven by the drive signal, and a ground level; the operation portion substrate 22 and the connector substrate 24 as substrates on which connectors such as the micro-connectors 31 and 35 that relay the wiring are provided; the comparison circuit 64 as voltage comparing means that compares the plurality of different power supply voltages; and the power supply control portion 66 as power supply control means that controls a supply of power to the image pickup device based on a comparison result of the voltage comparing means.

In the present embodiment, a plurality of power supply voltages that are supplied to the CCD 16 side as an image pickup device are respectively monitored, and it is determined whether or not the power supply wires 60*a* and 60*b* or power supply wires 60*a*' and 60*b*' are disconnected, or if an abnormal voltage has occurred due to a short circuit (or an insulation failure that falls short of being a short circuit) between connector contact pins of a small-size connector that relays any of the aforementioned power supply wires. If an abnormal state in which an abnormal voltage has occurred is determined, the power supply control portion 66 performs control to cut off the supply of power to the CCD 16, and also causes the notification signal generation circuit 67 to generate a notification signal that notifies the occurrence of an abnormal voltage and transmit the notification signal to the processor 4 side.

The control circuit 29 of the processor 4 outputs the notification signal to the signal processing circuit 28. The signal processing circuit 28 superimposes the notification signal upon a video signal. The monitor 5 displays the notification signal together with an endoscopic image. By means of the notification signal, the surgeon can quickly recognize that an abnormal voltage has occurred in the power supply voltage V1 or V2.

Accordingly, repairs or the like that correspond to the occurrence of the abnormal voltage can be swiftly performed on the endoscope 2A in which the abnormal voltage occurred to eliminate the abnormal state. Furthermore, continued usage in the abnormal state in which the abnormal voltage occurred (in this case, there is a possibility that a more serious abnormal state may occur) can be reduced, and usage of the endoscope 2A for a subsequent endoscopy in a state in which the abnormal state has not been repaired can be prevented.

Note that although information of threshold values for determining whether or not there is an abnormal voltage is previously stored in the ROM 65, a configuration may also be adopted in which the processor 4 side transmits information of threshold values for determining whether or not there is an abnormal voltage that is in accordance with the endoscope 2A that is actually connected to the processor 4 to the FPGA 51 side, and the FPGA 51 stores the information in the ROM 65.

In the case of this configuration, in an initial state or the like, the FPGA 51 of the endoscope 2A receives the above described threshold value information from the processor 4 side and performs a determination as to whether or not there is an abnormal voltage using that information. In a case where this configuration is adopted, threshold values can be set to more appropriate values even when the kind of the endoscope 2A or the like actually connected to the processor 4 for use is different (for example, when a size of a load with respect to a power supply is different).

By setting the threshold values to more appropriate values in this manner, with respect to the endoscope 2A or the like that is actually connected to the processor 4, it can be determined at an earlier stage that the voltage has changed from a normal state to an abnormal state in which the voltage is abnormal.

Although in the configuration example of the CCD power supply voltage monitoring circuit 63 shown in FIG. 4A, a configuration is adopted in which a comparison result of the comparison circuit 64 as voltage comparing means is outputted to the power supply control portion 66 as power supply control means, and the power supply control portion 66 controls the supply of power to the CCD 16 based on the comparison result of the comparison circuit 64, a configuration of a modification that is shown in FIG. 4B may also be adopted.

In a CCD power supply voltage monitoring circuit 63B shown in FIG. 4B, a configuration is adopted in which the comparison circuit 64 performs the control function of the power supply control portion 66 shown in FIG. 4A. In other words, the comparison circuit 64 as voltage comparing means is configured to also perform the function of the power supply control portion 66 as power supply control means.

In FIG. 4B, a configuration is adopted that, by means of the comparison results of the respective comparison circuits 64a and 64b included in the comparison circuit 64, controls the first constant voltage circuit 61a and the switch 61c, and the second constant voltage circuit 61b and the switch 61d, respectively, without employing the power supply control portion 66.

That is, when the comparison result of the comparison circuit 64a corresponds to an abnormal voltage, the comparison circuit 64a stops operation of the first constant voltage circuit 61a and turns the switch 61c off, to thereby cut off the supply of power to the CCD 16 side.

Further, when the comparison result of the comparison circuit 64b corresponds to an abnormal voltage, the comparison circuit 64b stops operation of the second constant voltage circuit 61b and turns the switch 61d off, to thereby cut off the supply of power to the CCD 16 side.

The comparison results of the comparison circuits 64a and 64b are outputted to the notification signal generation circuit 67, and if there is an abnormal voltage, the notification signal generation circuit 67 supplies a notification signal to the processor 4 side.

The remaining configuration is the same as that shown in FIG. 4A. The operations and/or effects of the modification shown in FIG. 4B are almost the same as the configuration shown in FIG. 4A, except that the voltage comparing means also performs the function of the power supply control means.

Note that the present invention is not limited to a configuration, as shown in FIG. 4A or FIG. 4B, that monitors a plurality of power supply voltages on an input side of the CCD power supply circuit 53b' that supplies the plurality of power supply voltages to the CCD 16, and a configuration may also be adopted that monitors a power supply voltage on an input side of a power supply circuit (for example, a CCD/TG power supply circuit 53b) that also supplies a power supply voltage to the TG 17 mounted in the distal end portion 14 together with the CCD 16, and cuts off the power that is supplied to the TG 17 if an abnormal voltage occurs, and notifies the occurrence of the abnormal voltage.

Further, in the case of an abnormal state in which a power supply that is supplied to the CCD 16 side and the TG 17 side is an excessive current (also referred to as "overcurrent" in the present specification), control may be performed so as to stop (shut down) the supply of power.

Figure 4C:
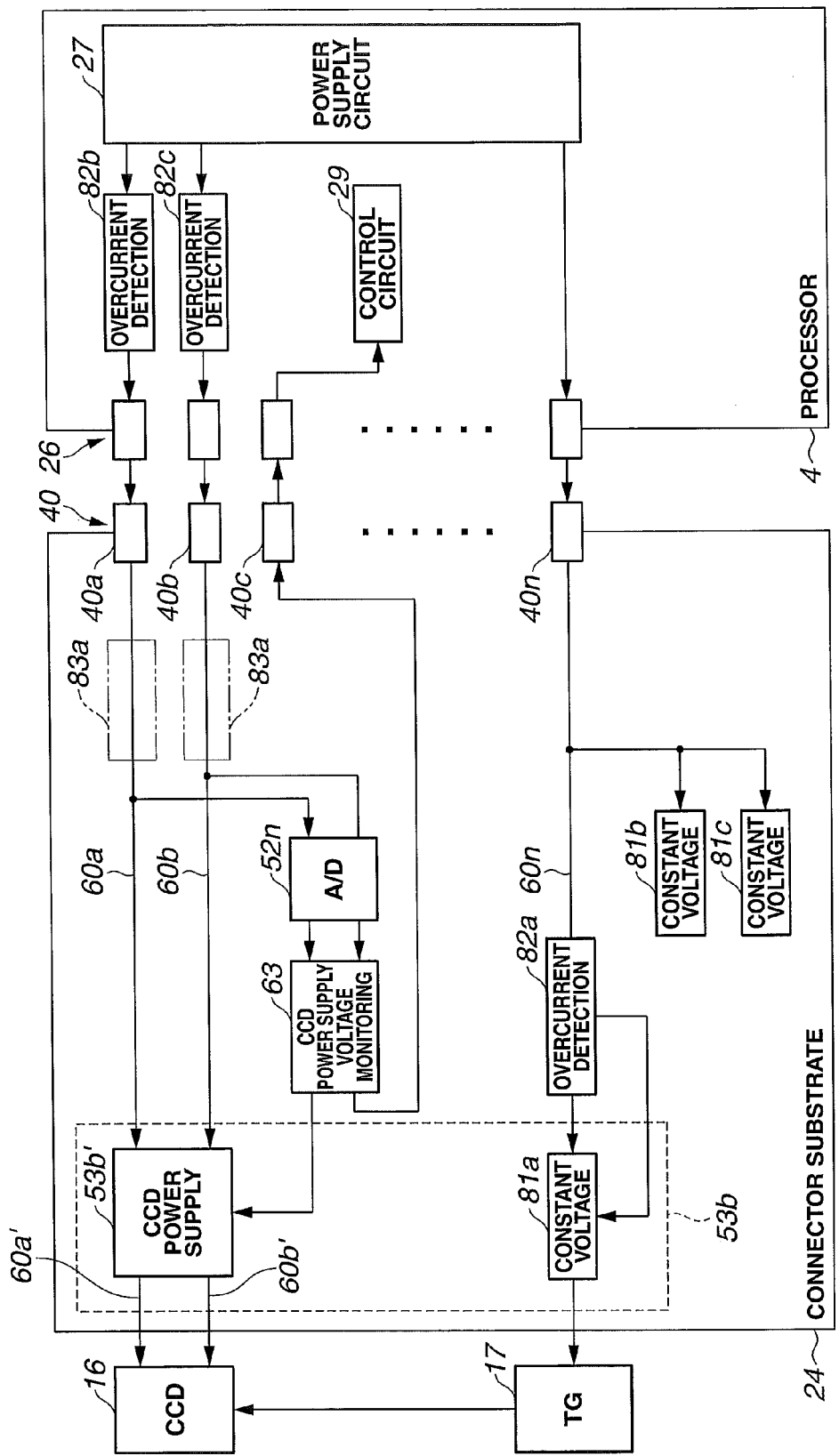
FIG. 4C is a view that illustrates a configuration in which, together with a CCD power supply voltage monitoring circuit, overcurrent detection circuits are provided that detect an overcurrent of a power supply voltage of a CCD and a timing generator.

FIG. 4C illustrates a configuration in which overcurrent detection circuits 82a to 82c are provided that detect whether or not a power supply that is supplied to the CCD 16 and a power supply that is supplied to the TG 17 are in an overcurrent state, and stop the supply of power if it is detected that the relevant power supply is in an overcurrent state.

In the configuration shown in FIG. 4C, the CCD power supply circuit 53b, the A/D conversion circuit portion 52n, and the CCD power supply voltage monitoring circuit 63 that were described above referring to FIG. 4A are provided in the connector substrate 24, and in addition thereto, a constant voltage circuit 81a that supplies power to the TG 17 and an overcurrent detection circuit 82a that detects an overcurrent at a stage prior to the constant voltage circuit 81a are provided in the connector substrate 24. Note that the overcurrent detection circuit 82a, for example, includes a comparison circuit that compares a voltage between both ends of a resistance value having a predetermined value that is connected in series with a power supply wire 60n with a predetermined voltage value that has been previously set for judging an overcurrent. If the comparison result indicates that the voltage between both ends of the resistance value is equal to or greater than the predetermined voltage value, the overcurrent detection circuit 82a detects that the state is an overcurrent state in which a current of the power supply that is supplied to the constant voltage circuit 81a is equal to or greater than a threshold value. The other overcurrent detection circuits 82b and 82c are configured in the same manner.

The overcurrent detection circuit 82a that is provided on the power supply wire 60n that is connected to a connector contact pin 40n shuts down the (current of) power supply that is supplied to the constant voltage circuit 81a side if an overcurrent that is equal to or greater than a previously set threshold value flows to the constant voltage circuit 81a side.

In FIG. 4C, a configuration is illustrated in which the overcurrent detection circuit 82a is provided only on the power supply wire 60n that should be monitored inside the endoscope 2A, and with respect to the other power supply wires 60a and 60b, the overcurrent detection circuits 82b and 82c for the CCD power supply circuit 53b are provided on the processor 4 side. If the overcurrent detection circuits 82b and 82c detect an overcurrent, a power supply that is supplied to the CCD power supply circuit 53b' side is shut down from the overcurrent detection circuits 82b and 82c.

Further, in the configuration shown in FIG. 4C, constant voltage circuits 81b and 81c are provided that supply power to electronic circuits inside the connector substrate 24. The CCD power supply circuit 53b' and the constant voltage circuit 81a correspond to the CCD/TG power supply circuit 53b shown in FIG. 3.

Note that judging voltage generation circuits 83a indicated by chain double-dashed lines that are provided on the power supply wires 60a and 60b are described later with reference to FIG. 4E.

A power supply circuit 27 in the processor 4 supplies power to the CCD power supply circuit 53b via the overcurrent detection circuits 82b and 82c, and also supplies power to the constant voltage circuits 81a to 81c.

An overcurrent detection circuit according to a conventional example is configured so as to repeat a sequence of operations in which the overcurrent detection circuit shuts down the current of a power supply that is supplied to the constant voltage circuit 81a upon detecting an overcurrent, cancels the shutdown state upon detecting a drop in the current due to the shutdown operation, and thereafter, when a state is entered in which an overcurrent flows, shuts down the current again upon detecting the overcurrent.

Therefore, the overcurrent detection circuit 82a that is adopted in the present embodiment is configured so that, upon detecting an overcurrent once, the overcurrent detection circuit 82a maintains the state in which the overcurrent has been detected until the power supply of the entire endoscope 2A is turned off, and thereby improves the above described sequence of the conventional example. Note that, the other overcurrent detection circuits 82b and 82c may also be configured to have the same functions as the overcurrent detection circuit 82a.

In the case of detecting an overcurrent by means of the overcurrent detection circuit 82a, a configuration may also be adopted that has a plurality of different threshold values in accordance with the kinds of the endoscope 2A, and that switches the threshold value in accordance with the endoscope 2A that is actually used (for example, threshold values may be switched in accordance with a difference in the external diameter of the endoscope 2A or a difference in the temperature at a distal end portion or the like). In this case, as specific means for switching threshold values, a resistor having a resistance value that depends on the kind of the endoscope 2A may be mounted inside the respective endoscopes 2A.

In addition, a digital trimmer for switching threshold values may be utilized, and a numerical value of the digital trimmer may be stored in a ROM. Further, with respect to the overcurrent protection circuits 82a to 82c, a configuration may be adopted in which the overcurrent protection circuits for the CCD and the TG are integrated into a single overcurrent protection circuit. Also, all of the overcurrent protection circuits 82a to 82c may be mounted inside the endoscope 2A, or may be mounted inside the processor 4 and not the endoscope 2A.

A configuration may also be adopted in which a ROM or a resistor is mounted in an image pickup unit that is unique to the endoscope 2A, and a detection circuit is configured to read out information of the mounted ROM or resistor. In addition, a configuration may be adopted in which the aforementioned ROM or the like is mounted in an MC substrate, an A/D substrate, an IF substrate or the like that is mounted in the endoscope 2A.

Figure 4D:
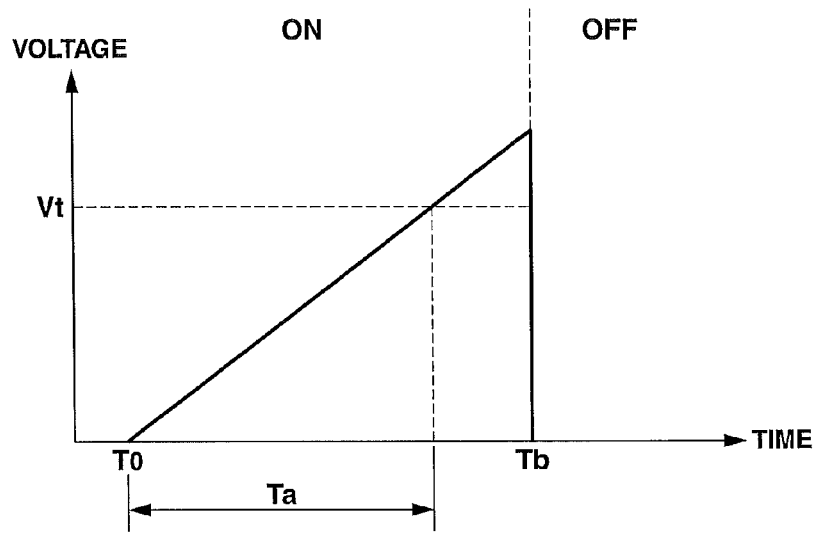
FIG. 4D is a view that illustrates a characteristic in a case of controlling operations to turn a power supply on/off inside an endoscope.

In the present embodiment, a configuration is adopted so as to perform control to turn the power supply on and off on the endoscope 2A side based on a characteristic illustrated in FIG. 4D. Note that, in FIG. 4D, the abscissa axis represents the time period and the ordinate axis represents the voltage.

FIG. 4D shows a characteristic whereby, the power supply on the endoscope 2A side is turned on after a time period Ta has passed from a time (timing) To at which the power supply on the processor 4 side was turned on, and on the other hand, when the power supply is turned off from a state in which the power supply was on, the power supply on the endoscope 2A side is turned off at almost the same timing as a time Tb at which the power supply is turned off or at a timing that is slightly later than the time Tb. Note that a voltage Vt indicates a threshold value at which the power supply is turned on or off.

By performing control based on this characteristic, in a case where the power supply is turned on/off on the processor 4 side, stable operation can be performed on the endoscope 2A side. When the power supply has been turned on, it is possible for a state to arise in which the power supply on the endoscope 2A side is repeatedly turned on/off at a fast timing because the state is one in which the signal connector 12 is not appropriately mounted to the processor 4 or in which a connection with a connector contact pin is not stable.

Consequently, if the power supply on the endoscope 2A side is also placed in an "on" state without waiting for a sufficient time period after the timing at which the power supply is turned on, stable operations can not be secured with respect to circuits to which the power is supplied because the circuits are actuated in a state in which the power supply is unstable.

Therefore, a configuration is adopted that can ensure stable operations on the endoscope 2A side by performing control that, when the power supply on the processor 4 side is turned on, turns the power supply on the endoscope 2A side on after a time period that is required in order to allow the power supply to stabilize (that is, place the power supply circuit on the endoscope 2A side in an operating state).

In contrast, in a case where the power supply on the processor 4 side has been turned off from a state in which the power supply was on, the power supply on the endoscope 2A side is turned off (the power supply circuit on the endoscope 2A side is shut down) after a short time period without taking a long time as in the case where the power supply is turned on. Note that a time period when the power supply is turned off after a short time period is a period of approximately a time T9 shown in FIG. 5B that is described later.

Figure 4E:
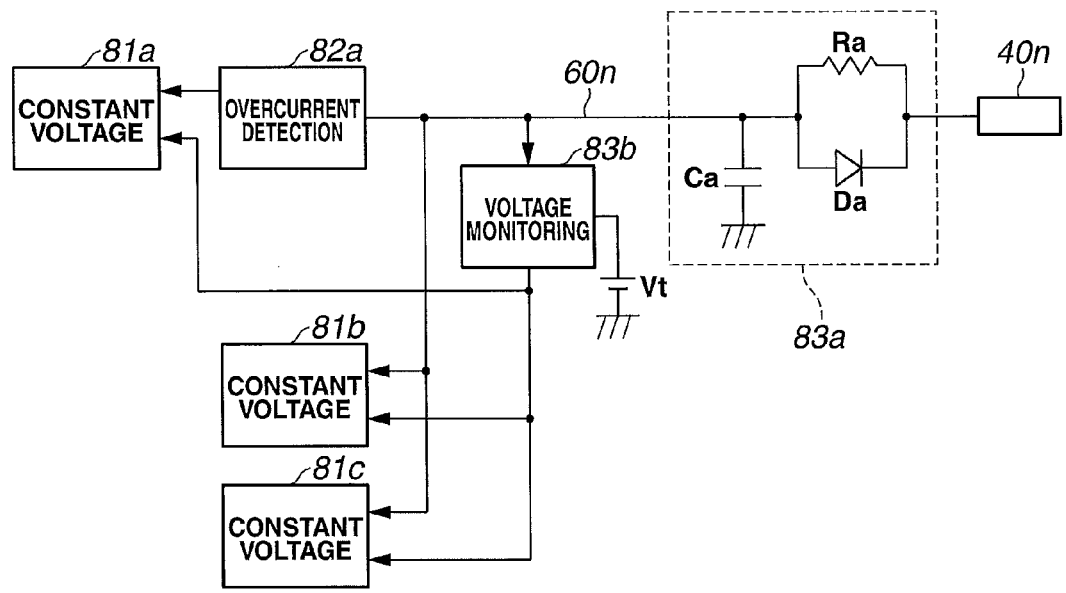
FIG. 4E is a view that illustrates a circuit configuration in a case controlling operations to turn a power supply on/off according to the characteristic illustrated in FIG. 4D.

When performing sequence control on the endoscope 2A side in the case of a configuration having the characteristic shown in FIG. 4D, for example, the sequence control may be implemented using a circuit configuration that is shown in FIG. 4E.

In FIG. 4E, the judging voltage generation circuit 83a that includes parallel circuit of a resistance Ra and a diode Da, and a capacitor Ca that is connected between an output terminal of the parallel circuit and a ground GND is provided, for example, on the power supply wire 60n connected to an input terminal of the overcurrent detection circuit 82a in FIG. 4C.

Further, in FIG. 4E, a voltage monitoring circuit 83b is provided that outputs a judging voltage generated by the judging voltage generation circuit 83a to the overcurrent detection circuit 82a, and also monitors the judging voltage and controls the on/off states of the power supply at each of the constant voltage circuits 81a, 81b, and 81c.

Note that a configuration may be adopted in which the overcurrent detection circuit 82a is equipped with the function of the voltage monitoring circuit 83b, and the voltage monitoring circuit 83b is omitted.

In the case of the configuration shown in FIG. 4E, when the power supply has been turned on at the processor 4 side, the current flows to the capacitor Ca via the resistance Ra, and the potential (voltage) of the capacitor Ca rises with time in accordance with a time constant between the resistance Ra and the capacitor Ca. Note that in this case the diode Da is in the reverse direction, and a resistance value thereof is sufficiently large compared to the resistance value of the resistance Ra.

The rising time constant in this case determines the characteristic in FIG. 4D (characteristic whereby the voltage rises with time). The voltage monitoring circuit 83b compares the voltage of the capacitor Ca (that is, a judging voltage generated by the judging voltage generation circuit 83a) and the threshold value Vt, and has a function of a power-on control circuit that, upon detecting a voltage that is equal to or greater than the threshold value Vt, controls to turn on the constant voltage circuits 81a, 81b, and 81c (or causes power to be outputted from the constant voltage circuits 81a, 81b, and 81c).

On the other hand, when the power supply on the processor 4 side is turned off from a state in which the power supply was on, the voltage of the connector contact pin 40n instantly drops to zero. Consequently, a charge accumulated in the capacitor Ca is released in a short time period by the diode Da that becomes the forward direction, the judging voltage of the capacitor Ca becomes less than or equal to the threshold value Vt in a short time period, and the voltage monitoring circuit 83b has a function of a power-off control circuit that controls so that the power supply of the constant voltage circuits 81a, 81b, and 81c is turned off in a short time period. By performing this control, stable operations can be ensured when the power supply has been turned on, and favorable responsiveness can be ensured with respect to when the power supply is turned off.

Note that the present invention is not limited to a case where the judging voltage generation circuit 83a is provided on the power supply wire 60n that is shown in FIG. 4E. For example, a configuration may also be adopted in which the judging voltage generation circuit 83a is provided on each of the other power supply wires 60a and 60b as indicated by chain double-dashed lines in FIG. 4C.

In the case of providing the judging voltage generation circuit 83a on each of the power supply wires 60a and 60b, the (power supply control portion 66 of the) CCD power supply voltage monitoring circuit 63 has the function of the voltage monitoring circuit 83b in FIG. 4E, and controls the on and off states of the power supply of the CCD power supply circuit 53b' using the characteristic that was described above referring to FIG. 4D.

In this case, in addition to the control function (first control function) described in FIG. 4A and FIG. 4C, the power supply control portion 66 has a control function (second control function) that controls on and off states of the power supply of the CCD power supply circuit 53b' with respect to a case where the power supply has been turned on/off on the processor 4 side.

Further, a configuration as shown in FIG. 5A may be adopted as a cable driving method in a case of driving the CCD 16 from the FPGA 51 via the TG 17, to thereby improve the bluntness of a waveform.

The FPGA 51 generates HDR_CLK, HDR_CLK_N, HDR_HBLK as, for example, three clocks that the TG 17 requests. The clocks HDR_CLK, HDR_CLK_N, and HDR_HBLK that are outputted from the FPGA 51 drive buffers 85a included in cable drive circuits, and respective coaxial cables that constitute the integrated coaxial cables 21 and 23 via peaking circuits 86 that are respectively formed of a parallel circuit of a capacitor 86a and a resistance 86b.

A configuration is adopted in which a plurality of the buffers 85a are connected in parallel in accordance with the clocks so that it is possible to satisfy a required drive current specification. Specifically, in the case of the HDR_CLK clock, three buffers 85a are parallelly connected, in the case of the HDR_CLK_N clock also, three buffers 85a are parallelly connected, and in the case of the HDR_HBLK clock, two buffers 85a are parallelly connected, so that a drive current that can be driven with a single buffer 85a can be increased several-fold.

Further, an emphasized waveform (illustrated in the drawing with respect to the case of HDR_CLK) obtained by differentiation of a rising waveform and a falling waveform portion of each clock is formed by the peaking circuit 86, and after the waveform has been blunted by the coaxial cable, a clock waveform that is close to a rectangular wave can be supplied to the TG 17.

Note that a value of the capacitor 86a and the resistance 86b of the peaking circuit 86 is switched or is set to an appropriate value in accordance with the kind of the endoscope 2A.

Further, as the three clocks that are outputted from the FPGA 51, in some cases the TG 17 requests that the clocks are identical with a frequency of a clock the FPGA 51 received from the processor 4 and are clocks for which the duty is 50%.

Therefore, after doubling the clock that is received from the processor 4, the FPGA 51 divides the clock in half to generate a clock for which the duty is 50%.

Note that although FIG. 5A illustrates an example in the case of the three clocks HDR_CLK, HDR_CLK_N, and HDR_HBLK, this corresponds to the case of the two pulse signals φH and φV in the case of the endoscope 2B in FIG. 2B, and it is clear that the configuration can be similarly applied in this case also. Further, in the case of the endoscope 2A, as shown in FIG. 3, four pulses (φH and φV of LVDS) are sent from the FPGA 51 to the operation portion 7 and the two pulse signals φH and φV are sent from the operation portion 7 to the TG 17, and the configuration can also be applied in this case.

The FPGA 51 also includes an unshown counter circuit into which is inputted an H reset signal that resets a CCD discrimination signal, a vertical synchronizing signal VD, or a horizontal synchronizing signal. Signals such as a horizontal clock HCLK, a vertical clock VCLK, and a clamp pulse OBCLP that clamps the potential in the optical black portion (black level) of the CCD 16 are generated with this counter circuit.

Further, the FPGA 51 includes a control signal generation circuit (for example, SCP_SEQ) that generates power supply control signals (+5V_AFE1 and −5V_AFE1) for the first analog circuit 53c and power supply control signals (+5V_AFE2 and −5V_AFE2) for the second analog circuit 53h and the like based on the pulse signal of SC-CLK_EN described with reference to FIG. 3, a signal SDWN that is used when turning on/off the driving of the above described HCLK and the like, VD_INT as a vertical synchronizing signal for internal operations of the FPGA 51, the horizontal synchronizing signal HD, and a signal that passed through the LPF and the like.

In a case where a user turned the power supply on/off on the processor 4 side, the processor 4 transmits SC-CLK_EN as a pulse signal that detected that operation to the FPGA 51 inside the endoscope 2A. The FPGA 51 uses the SC-CLK_EN signal to perform on/off control of various kinds of power supplies at a predetermined timing in the endoscope 2A and control of a CCD drive signal.

By performing on/off control of various kinds of power supplies and control of a CCD drive signal utilizing a pulse signal that detected that the power supply was turned on/off in this manner, control that corresponds to the power supply being turned on/off can be swiftly executed. That is, although a delay of a time period until communication is established arises when utilizing communication between the processor 4 and the FPGA 51 inside the endoscope 2A, by utilizing a pulse signal that detected that the power supply was turned on/off from the processor 4 side to the FPGA 51 side, favorable responsiveness can be secured without almost any occurrence of the aforementioned delay time period.

Figure 5B:
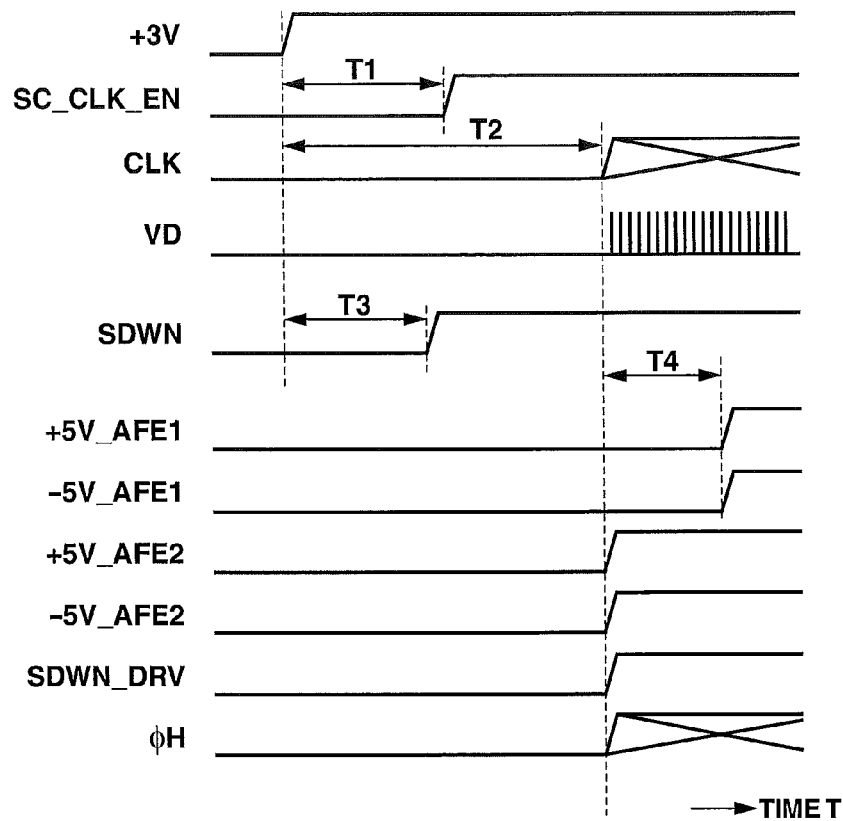
FIG. 5B is a view that illustrates timings at which control to turn a power supply on/off and the like is performed on an endoscope side based on a specific pulse signal that is sent from a processor side when the power supply is turned on/off.

As shown in FIG. 5B, a clock CLK at a predetermined timing, the vertical synchronizing signal VD, SDWN that controls on/off of various signals, the power supply control signals for the first analog circuit 53c (+5V_AFE1 and −5V_AFE1), the power supply control signals for the second analog circuit 53h (+5V_AFE2 and −5V_AFE2), SDWN-DRV that turns ϕH as a drive signal that drives the CCD 16 on/off, and the horizontal transfer signal ϕH (and unshown ϕV) are controlled utilizing the above described SC-CLK_EN pulse signal at a time of turning the power supply on and at a time of turning the power supply off.

When turning on the power supply, if a power supply of a predetermined voltage (for example, 3V) is turned on, after a time period T1 (for example, approximately 400 ms) from when the power supply is turned on, SC-CLK_EN rises to H level from L level, and after a time period T2 (for example, approximately 1000 ms) the clock CLK enters an operating state and in synchrony therewith a state is entered in which the vertical synchronizing signal VD is also outputted, +5V_AFE2, −5V_AFE2, and SDWN_DRV also rise to H level, and ϕH is also outputted.

Further, SDWN rises after a time period T3 (for example, approximately 400 ms) from the aforementioned power on time.

In addition, +5V_AFE1 and −5V_AFE1 rise to H level after a time period T4 (for example, 500 ms) from when the clock CLK entered the operating state. The timing at which outputting of ϕH stops is a stopping timing that is synchronous with HD that is being generated inside the FPGA 51. It is thereby possible to prevent an unstable ϕH pulse from being generated and to stably stop ϕH. A configuration may also be adopted that stops ϕH in synchrony with VD, and not HD.

On the other hand, at a time when the power supply is turned off, first SC-CLK_EN falls to L level from H level, and after a time period T5 (for example, approximately 300 μs) from the timing at which SC-CLK_EN falls, SDWN_DRV falls and outputting of ϕH also stops.

Further, after a time period T6 (for example, 15 ms) from the timing at which SC-CLK_EN falls, −5V_AFE1 and −5V_AFE2 fall to H level, and after a time period T7 (for example, 20 ms) from the timing at which SC-CLK_EN falls, +5V_AFE1 and +5V_AFE2 rise to H level, and after a time period T8 that is a timing somewhat after that, CLK stops, and after a time period T9 (approximately 40 ms to 50 ms) after CLK stops, the power supply of the predetermined voltage is turned off.

The configuration that is adopted can ensure favorable responsiveness particularly when the power supply is turned off, by placing the power supply in an off state after a shorter time period than when the power supply is turned on. In addition, at both a time the power supply is turned on and a time the power supply is turned off, by performing control based on SC-CLK_EN, favorable responsiveness can be ensured compared to a case that utilizes communication.

Note that in a case that utilizes communication also, if the required responsiveness can be realized, a configuration may be adopted that performs the above described control utilizing communication. Further, a configuration may also be adopted in which detection means is provided that detects when the power supply is turned on and off at the endoscope 2A side, and that performs the above described control utilizing a detection signal of the detection means.

Note that an integrated circuit (IC) such as the FPGA 51 that is mounted on the endoscope 2A side has a tolerant function such that a circuit is not damaged even in a case where the order of inputting power and a signal is reversed.

As described in FIG. 5B also, for example, in a case where the power supply has been turned on, although in the endoscope 2A control is performed so that the clock CLK and the like rises (is inputted) after power has been supplied, even in a case where the timing of that control has been reversed due to some kind of cause, an IC such as the FPGA 51 is protected so as not to be damaged by the tolerant function.

That is, the endoscope 2A has an interface that includes the tolerant function and is configured so that an IC or the like on the endoscope 2A side is not damaged.

Figure 5C:
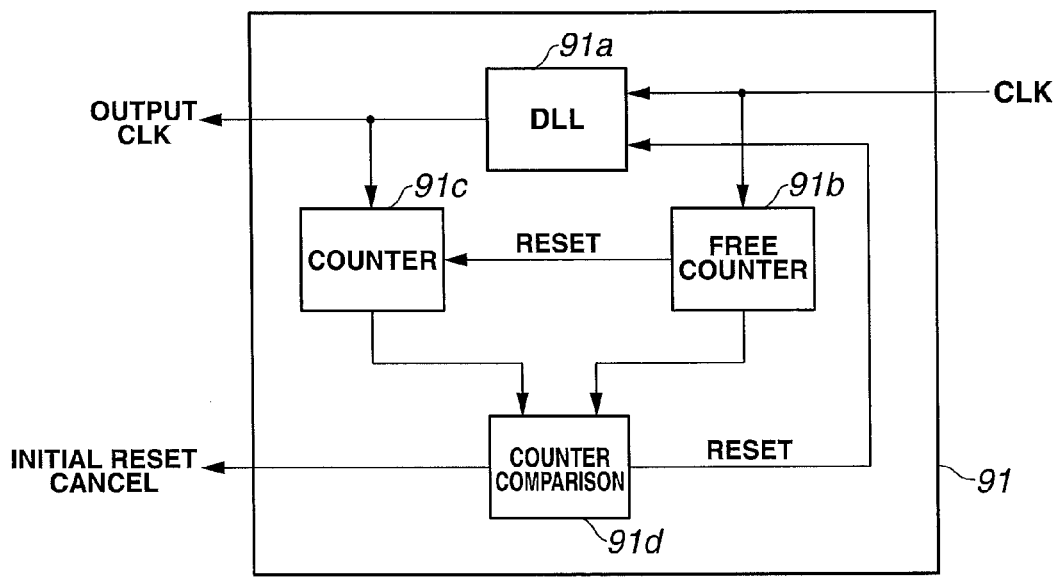
FIG. 5C is a view that illustrates the configuration of a CLK determination and judgment circuit that performs operations to determine a clock signal when generating an output clock that corresponds to a clock signal that is inputted from a processor side.

Further, as shown in FIG. 5C, the FPGA 51 has a CLK determination and judgment circuit 91 that performs a CLK determination operation that determines the CLK at a starting time of the clock CLK that is inputted from the processor 4 side at a starting time when the power supply is turned on, and also performs a CLK abnormality judgment.

The CLK that is inputted from the processor 4 side is inputted to a DLL (delay-locked loop) 91a that adjusts a delay amount and is also inputted to a free counter 91b. The DLL 91a generates and outputs an output CLK as a clock signal that tracked the inputted CLK.

The output CLK that is outputted from the DLL 91a is supplied as the CLK to the FPGA 51 and other circuits, and is also inputted to a counter 91c. Note that, when starting a count operation, the free counter 91b resets the counter 91c, and controls so that the two counters count the CLK and the output CLK at the same timing.

The respective count values of the free counter 91b and the counter 91c are inputted to a counter comparison circuit 91d. If the count values of both counters are within a predetermined range at a predetermined timing, the counter comparison circuit 91d judges that the output CLK that is outputted from the DLL 91a is stable.

In the case of this judgment result, the counter comparison circuit 91d applies a signal that cancels the (initial) reset to each circuit that operates in synchrony with the output CLK and causes each of the circuits to perform operations that are synchronized with the output CLK. A configuration may also be adopted in which, if the DLL 91a is unstable after starting also, and not just at the time of starting, reset is cancelled after the DLL 91a stabilizes.

In contrast, if the count values of both counters are not within the predetermined range, the counter comparison circuit 91d judges that the inputted CLK or operation of the DLL 91a is abnormal, and resets the DLL 91a.

When generating the output CLK using the DLL 91a with respect to the inputted CLK in this manner, the CLK determination and judgment circuit 91 is formed in which a function is added that supplements the features of the DLL 91a.

By means of the CLK determination and judgment circuit 91 shown in FIG. 5C, for example, in a case where the DLL 91a hangs due to a disturbance caused by static electricity or the like and the output CLK that is outputted from the DLL 91a is constantly abnormal, the DLL 91a can be reset and controlled so as to perform normal operations. Further, in some cases the frequency of the output CLK becomes unstable for a predetermined period when there is a fluctuation in the frequency or phase of the inputted CLK. However, in such case also, the DLL 91a is reset and controlled so as to perform stable operation.

In addition, in the case of the above described configuration, if the output CLK of the DLL 91*a* was stable at the time of starting also, each circuit to which the output CLK that the DLL 91*a* outputs is supplied can be caused to start stable operations at once.

Further, a delay that is due to a transmission cable on the way to the endoscope 2A arises in the SC-CLK_EN pulse signal, the clock, the synchronizing signal and the like shown in FIG. 5B that are inputted into the endoscope 2A from the processor 4 side, and phase shifts arise with respect to each other. Therefore, a configuration may also be adopted that absorbs the influence of such phase shifts to enable the performance of stable operations.

Figure 5D:
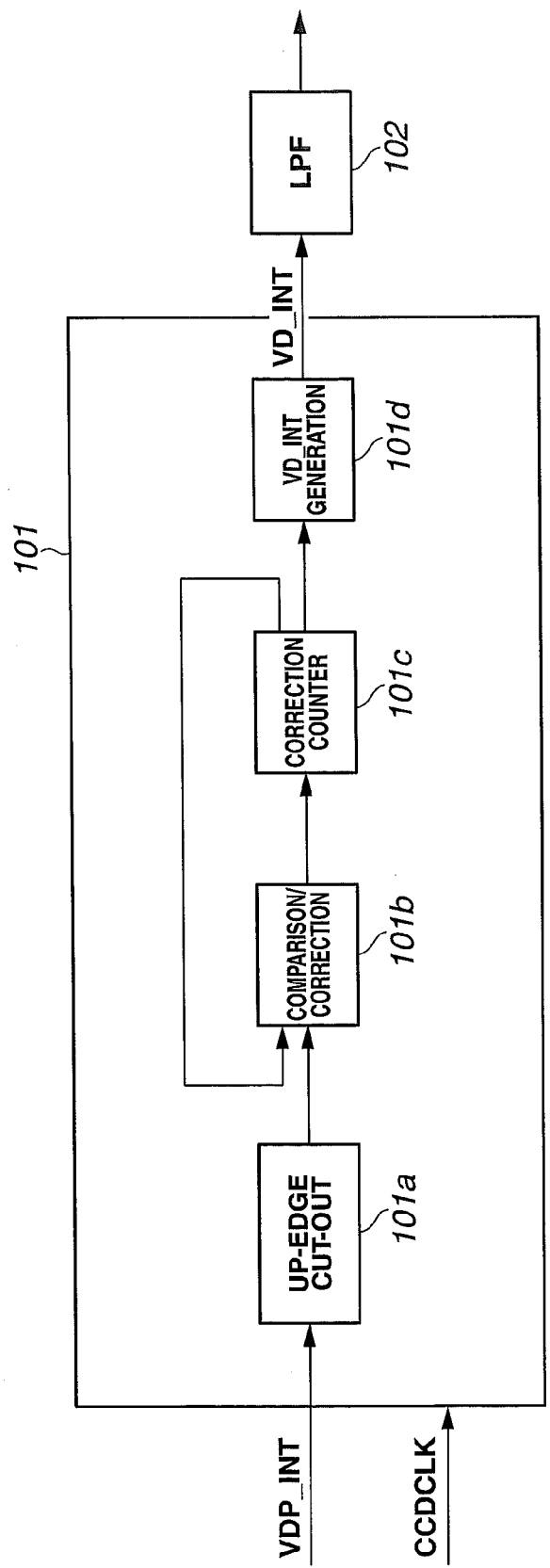
FIG. 5D is a block diagram that illustrates the configuration of a vertical synchronizing signal output circuit.

FIG. 5D illustrates a configuration of a vertical synchronizing signal output circuit 101 that outputs, for example, a vertical synchronizing signal VD_INT that has absorbed the influence of a phase shift with respect to a vertical synchronizing signal VDP_INT that is inputted to the FPGA 51 from the processor 4 side.

An up-edge of the VDP_INT signal that is inputted to the vertical synchronizing signal output circuit 101 from the processor 4 is cut out in synchrony with CCDCLK as a CCD clock by an up-edge cut-out circuit 101*a*, and operations of a comparison/correction circuit 101*b* that performs comparison and correction in the up-edge period are activated. Although in this case an example is described in which the up-edge cut-out circuit 101*a* that cuts out an up-edge is used, a configuration may also be adopted that uses a down-edge cut-out circuit that cuts out a down-edge instead of the up-edge cut-out circuit 101*a*.

Note that the CCDCLK signal is inputted to each circuit in the vertical synchronizing signal output circuit 101, and each circuit operates in synchrony with the CCDCLK signal.

For each vertical synchronizing signal VD period, a count value of the correction counter 101*c* that counts (measures) a predetermined number (N in FIG. 5E) of the CCDCLK signals is inputted to the comparison/correction circuit 101*b*. The correction counter 101*c* outputs the count value obtained by counting the predetermined number of CCDCLK signals to the comparison/correction circuit 101*b*, and also outputs a pulse at a timing at which the predetermined number of CCDCLK signals was counted to a VD_INT generation circuit 101*d*.

The VD_INT generation circuit 101*d* outputs a vertical synchronizing signal VD_INT that absorbed a phase shift to each circuit inside the endoscope 2A including the FPGA 51 in synchrony with the output of the correction counter 101*c*.

In the up-edge period, the comparison/correction circuit 101*b* compares the count value of the correction counter 101*c* and the predetermined number, and corrects a count operation of the correction counter 101*c* in accordance with the comparison result.

The VD_INT generation circuit 101*d* generates a vertical synchronizing signal VD_INT that is synchronized with a pulse that is outputted from the correction counter 101*c*, and outputs the vertical synchronizing signal VD_INT to a LPF circuit 102 that uses a low-pass filter that reduces disturbance. The vertical synchronizing signal VD_INT in which noise that is the disturbance has been reduced is supplied from the LPF circuit 102 to each circuit inside the endoscope 2A including the FPGA 51.

FIG. 5E illustrates a timing chart for the operations in FIG. 5D. The phase of the vertical synchronizing signal VDP_INT that is actually inputted to the vertical synchronizing signal output circuit 101 inside the endoscope 2A is delayed relative to the vertical synchronizing signal VD that is generated on the processor 4 side.

An up-edge at which the vertical synchronizing signal VDP_INT shifts upward in synchrony with the CCDCLK is cut out by the up-edge cut-out circuit 101*a*, and the comparison/correction circuit 101*b* becomes active in the up-edge period thereof and compares the count value of the correction counter 101*c* with the predetermined number.

When a phase difference between the vertical synchronizing signal VD and the vertical synchronizing signal VDP_INT is in a standard state, the count value is the predetermined number N, and the comparison/correction circuit 101*b* causes a count operation of the correction counter 101*c* to be performed with the predetermined number N maintained as it is. That is, in this case, the comparison/correction circuit 101*b* does not perform a correction of the count operation of the correction counter 101*c*. At this time, the correction counter 101*c* is reset to 0 at the up-edge.

On the other hand, if a phase shift (delay) of the vertical synchronizing signal VDP_INT relative to the vertical synchronizing signal VD is 1 count, the comparison/correction circuit 101*b* sets the correction counter 101*c* to 1 (in practice, so as to count for the corrected N+1 times) and causes the correction counter 101*c* to perform the count operation.

In contrast, if a phase shift (advance) of the vertical synchronizing signal VDP_INT relative to the vertical synchronizing signal VD is 1 count, the comparison/correction circuit 101*b* sets the correction counter 101*c* to N (so as to count N−1 times) and causes the correction counter 101*c* to perform the count operation.

By causing operations to be carried out in this manner, when a phase shift is within a range to the extent of ±1 clock of CCDCLK, it is possible to generate a stable vertical synchronizing signal VDP_INT that has absorbed the phase shift. In the case of a phase difference that is equal to or greater than ±1 clock of CCDCLK, the comparison/correction circuit 101*b* always resets the correction counter 101*c* to 0 at an active time.

Figure 6A:
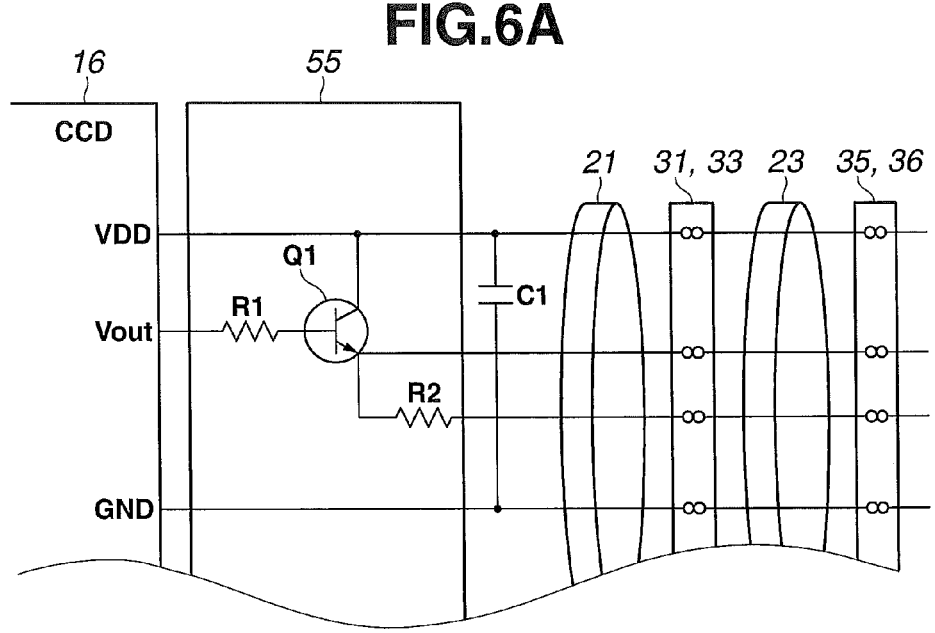
FIG. 6A is a view that illustrates a structure in which a cable that is connected to a CCD is relayed via micro-connectors.

FIG. 6A illustrates a configuration in the vicinity of the integrated coaxial cables 21 and 23 that transmit the output signal of the CCD 16 and the like and an MC connection portion. Note that, the MC connection portion represents an MC and an MC receptacle that is connected to the MC. In the configuration in FIG. 6A, the MC connection portion includes the MC 31 and the MC receptacle 33, and the MC 35 and the MC receptacle 36.

A power supply terminal to which a power supply voltage VDD is supplied in the CCD 16 is described simply as "power supply terminal VDD". The power supply terminal VDD undergoes an MC connection (relay) at the MC 31 and the MC receptacle 33 via a power supply wire included in the integrated coaxial cable 21 connected to the distal end portion substrate 18. And thereafter the power supply terminal VDD is connected with the CCD/TG power supply circuit 53*b* (see FIG. 3) of the IF substrate 24A via a power supply wire included in the integrated coaxial cable 23 after undergoing an MC connection at the MC 35 and the MC receptacle 36.

Further, a CCD output terminal Vout that outputs a CCD output signal Vout of the CCD 16 is connected to the base of a transistor Q1 included in the transistor array 55 via a resistance R1 mounted in the distal end portion substrate 18. The collector of the transistor Q1 is connected to the power supply terminal VDD, and the emitter thereof becomes the signal output terminal Vout according to an emitter follower, and is also connected to an output signal ground GND (Vout) via a resistance R2. Further, the power supply terminal VDD and the ground GND are connected via a capacitor C1.

The signal output terminal Vout according to the emitter follower is connected to the amplifier 53*d* of the IF substrate 24A by a signal wire that transmits an image pickup signal that is included in the integrated coaxial cables 21 and 23 similarly to the case of the power supply wire connected to the power supply terminal VDD that is described above, after being relayed en route by an MC connection.

The output signal ground GND (Vout) is also connected to an unshown output signal ground GND (Vout) of the IF substrate 24A by a ground signal wire that transmits (conveys) a ground level similarly to the case of the signal wire of the signal output terminal Vout that is described above.

The ground GND is also connected by means of a ground wire to an unshown ground GND of the IF substrate 24A after being relayed en route by an MC connection similarly to the case of the power supply wire that is described above.

Note that FIG. 6A shows one channel portion in the transistor array 55 shown in FIG. 3, and the same configuration can also be applied for the other three channels.

Figure 6B:
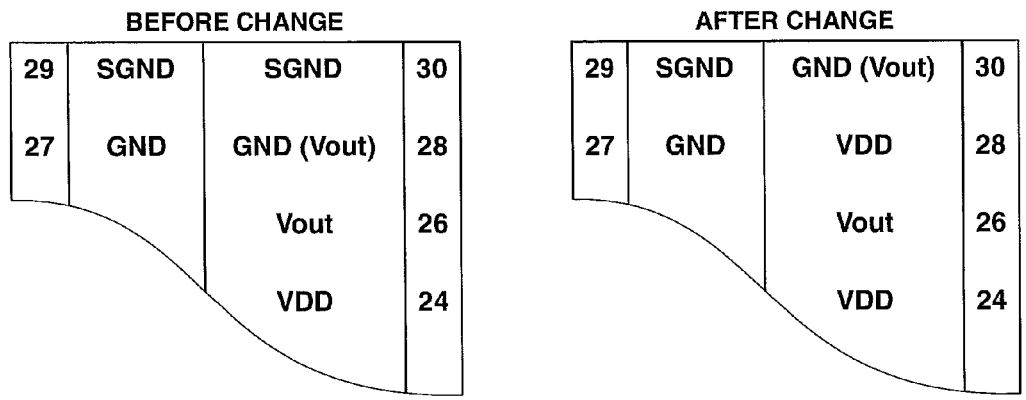
FIG. 6B is a view that illustrates an example of the arrangement of connector contact pins in a case of relaying various signal wires by means of a micro-connector.

In the present embodiment, the arrangement of connector contact pins that connect the various signal wires and the like by an MC connection is changed from a pre-change arrangement to a post-change arrangement as shown in FIG. 6B. In the pre-change MC connection example, a connector contact pin denoted by reference number 30 is connected to a shield ground SGND, a connector contact pin denoted by reference number 28 that is adjacent thereto is connected to the output signal ground GND (Vout), a connector contact pin denoted by reference number 26 that is adjacent to the connector contact pin 28 is connected to the signal output terminal Vout, and a connector contact pin denoted by reference number 24 that is adjacent to the connector contact pin 26 is connected to the power supply terminal VDD.

In contrast, in the post-change arrangement of the connector contact pins that connect the various signal wires by an MC connection, the connector contact pin denoted by reference number 30 is connected to the output signal ground GND (Vout), the connector contact pin denoted by reference number denoted by reference number 28 is connected to the power supply terminal VDD, the connector contact pin denoted by reference number 26 is connected to the signal output terminal Vout, and the connector contact pin denoted by reference number 24 is connected to the power supply terminal VDD.

In the arrangement state in which the various signal wire are connected by means of the connector contact pins before the change, since the output signal ground GND (Vout) had been arranged adjacent to the signal output terminal Vout, if these short-circuit, an overcurrent will flow to the transistor Q1 shown in FIG. 6A, and in such case, the overcurrent protection circuit on the processor 4 side will detect the overcurrent and shut down the power supply of the power supply terminal VDD.

However, in a case where a state between adjacent connector contact pins falls short of a complete short-circuit state in this manner and an image is outputted, for example, if the state in one in which a short circuit occurs at a resistance value of approximately 200 ohms, a state is entered in which the overcurrent protection circuit can not detect the current as an overcurrent, and the overcurrent continues to flow to the transistor Q1 and generation of heat continues.

Therefore, in the present embodiment, as shown in the post-change arrangement, the arrangement is changed so as to arrange the power supply terminal VDD adjacent to the signal output terminal Vout, and to connect the output signal ground GND (Vout) using the connector contact pin denoted by reference number 30.

In this arrangement, since an image is no longer outputted normally if the signal output terminal Vout enters a short-circuit state or a state that is near to a short circuit with the power supply terminal VDD, the user can recognize this situation at once as an image abnormality. Furthermore, since an overcurrent does not flow to the transistor Q1 in this case, the possibility of the transistor Q1 or the CCD 16 developing a fault due to heat generation can be reduced.

The present embodiment is configured so as to facilitate swift recognition of the occurrence of a short circuit by changing the arrangement in the case of connecting the various signal wires by means of MC connections as described above. According to the present embodiment, in a case where the various signal wires are soldered to the MC and MC receptacle, coating is performed to cover the locations that were soldered with a resin, to thereby form a structure that more effectively prevents the occurrence of short circuits and the like.

Figure 7:
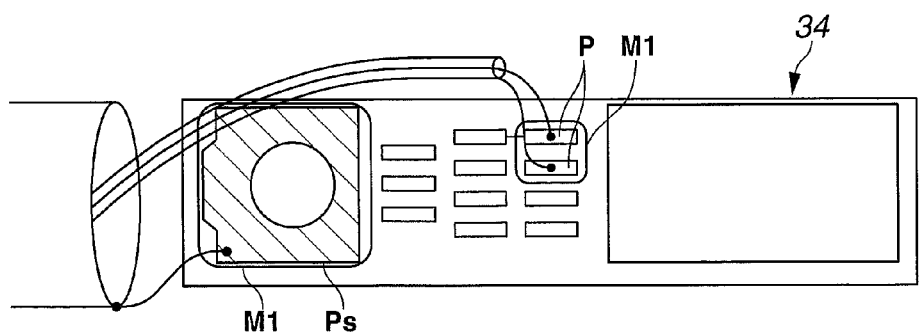
FIG. 7 is an explanatory drawing showing a manner in which solder portions of various signal wires are coated with resin on a micro-connector substrate.

FIG. 7 illustrates, for example, a back surface of the MC substrate 34. An integrated shield of the integrated coaxial cable 21 shown in FIG. 2A is soldered to a pad Ps for the shield ground SGND, and is covered (coated) with an insulative resin M1. Note that the integrated shield may also be crimped with a mechanical member, or may be fixed with a mechanical member that can be soldered.

Similarly, a pad P to which signal wires (central conductors) of various coaxial signal wires in the integrated coaxial cable 21 are connected by soldering, and a pad P to which an external shield wire is connected by soldering are also covered with the insulative resin M1. Although only one portion is shown in FIG. 7, solder portions at the remaining pads P are also covered in a similar manner with the insulative resin M1.

Figure 8A:
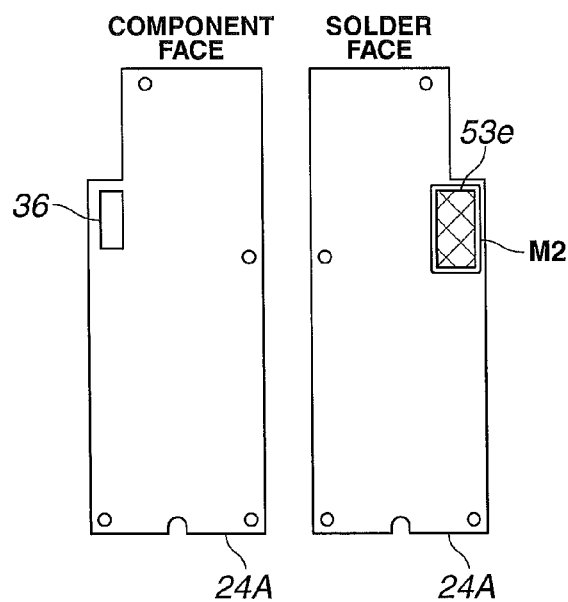
FIG. 8A is an explanatory drawing showing a manner in which an exposed circuit portion of a print pattern is coated with resin on an interface substrate.

FIG. 8A shows a component face and a solder face (back surface) of the IF substrate 24A in the connector substrate 24. The MC receptacle 36 to which the MC 35 connects is provided on the component face.

On the solder face, since a wiring portion of a print pattern is exposed at an input circuit portion 53*e* indicated by crosshatching that serves as a pre-stage portion of the amplifier 53*d* (see FIG. 3) into which the output signal Vout is inputted, a configuration is adopted in which the input circuit portion 53*e* is covered (coated) with an insulative resin M2. Note that the same resin can be used for the resins M1 and M2.

Figure 8B:
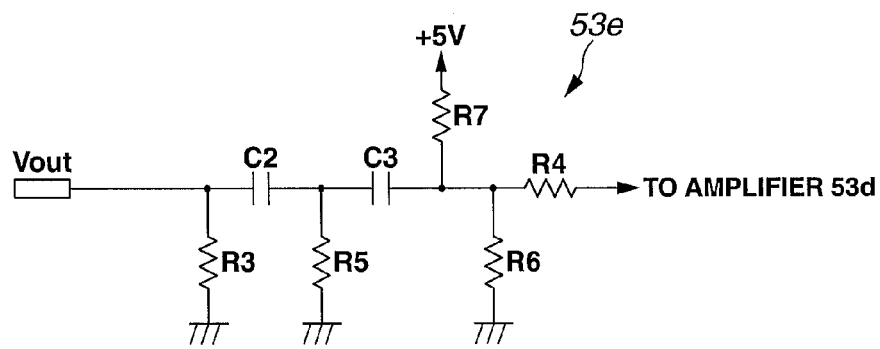
FIG. 8B is a view illustrating a circuit configuration of an input circuit portion that is coated with resin that is shown in FIG. 8A.

FIG. 8B illustrates the circuit configuration of the input circuit portion 53*e*. The output signal Vout that is inputted into the input circuit portion 53*e* via the MC 35 is grounded via a resistance R3 and is also inputted to the amplifier 53*d* via a series circuit of capacitors C2 and C3 and a resistance R4. A connecting point between the capacitors C2 and C3 is grounded via a resistance R5. Further, a connecting point between the capacitor C3 and the resistance R4 is grounded via a resistance R6 and is also connected to a predetermined power supply terminal (+5V) via a resistance R7.

By covering the print pattern that is exposed as a signal wire that transmits the output signal Vout with the insulative resin M2 as described above, it is possible to effectively prevent a situation in which an insulation failure occurs at the print pattern due to moisture or the like. A configuration may also be adopted in which all circuits at which an insulation failure may occur due to the influence of moisture or the like and at which heat generation or heat damage (thermal burn) may occur are coated with insulative resin, and not just a signal wire that transmits the output signal Vout.

Figure 8C:
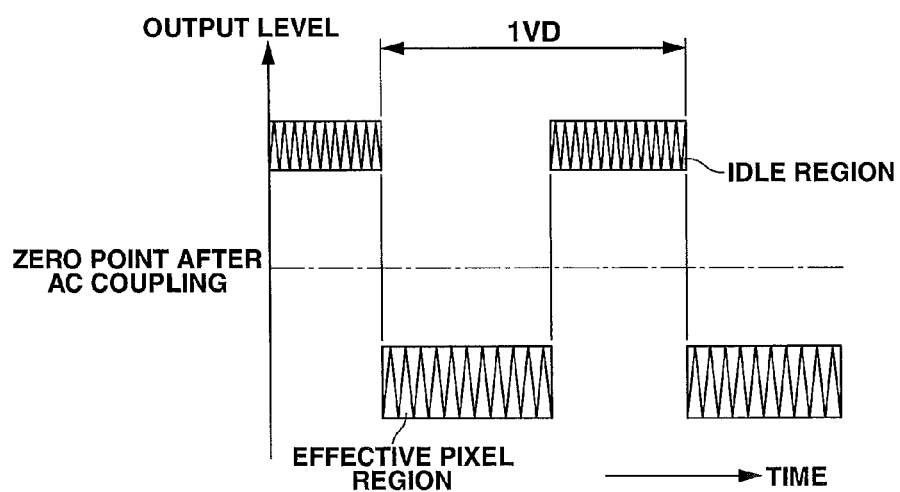
FIG. 8C is a view that illustrates a waveform of a CCD output signal that is inputted to an amplifier when a CCD is intermittently driven.

In the present embodiment the CCD 16 is subjected to intermittent driving. Specifically, as shown in FIG. 8C, since the CCD 16 is subjected to intermittent driving in which one vertical synchronizing period (denoted by "1VD") is taken as a cycle, a DC level of the CCD output signal Vout fluctuates. In a drive period in which the DC level becomes low the CCD output signal Vout includes a signal of an effective pixel region, and in an idle period in which the DC level becomes high, the CCD output signal Vout is a signal of an idle region and not an effective pixel region.

If the CCD output signal Vout is inputted as it is to the amplifier 53d via the input circuit portion 53e as described above, the CCD output signal Vout exceeds an allowable range of an input signal on the subsequent stage side of the amplifier 53d. Therefore, as the amplifier 53d in the present embodiment, a circuit configuration is adopted that, utilizing the fact that the DC level fluctuates as shown in FIG. 8C, clips a signal of an idle region and selectively amplifies only a signal of an effective pixel region.

Figure 8D:
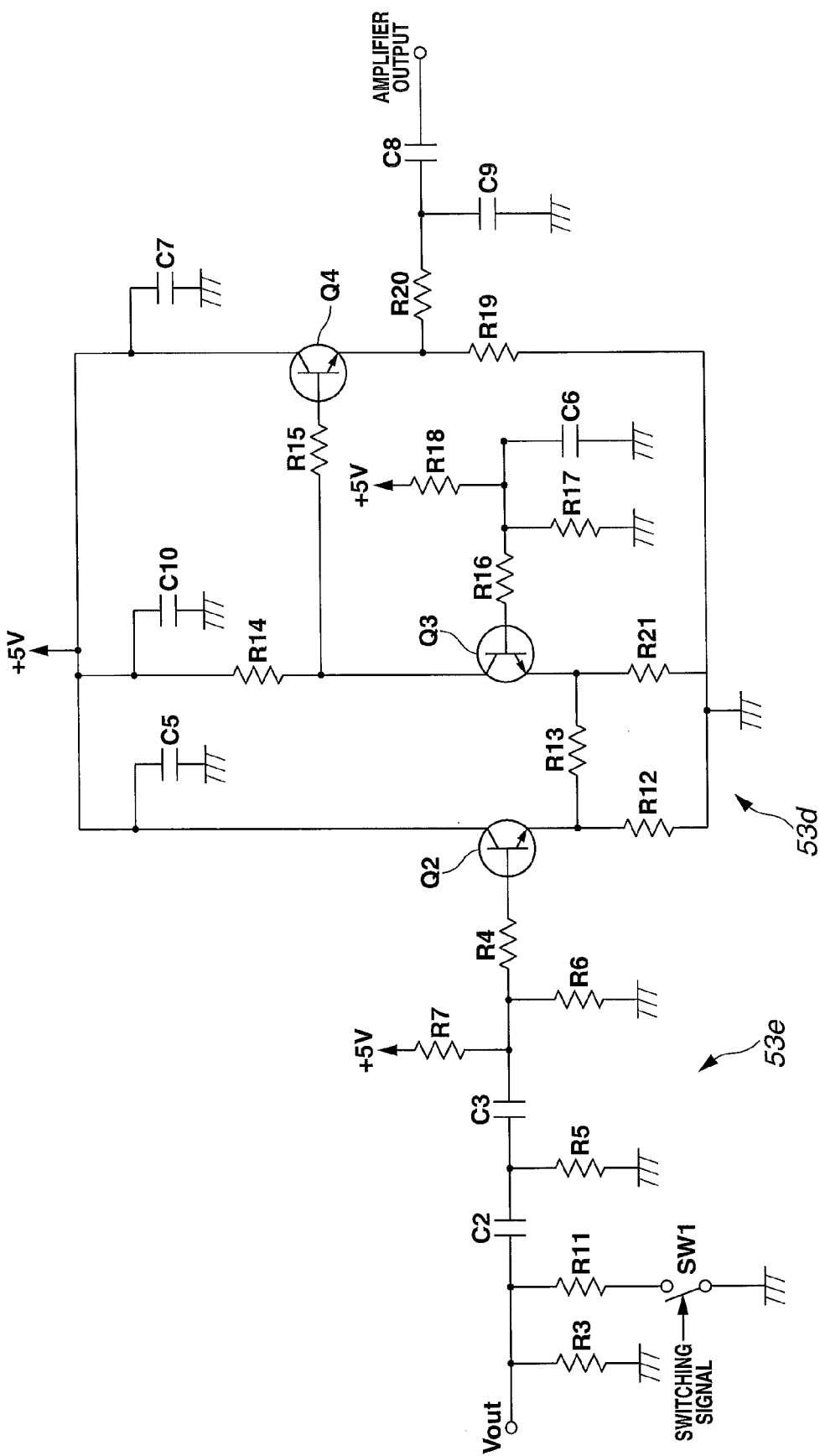
FIG. 8D is a view that illustrates a circuit configuration of an amplifier that clips a signal of an idle region and amplifies a signal of an effective pixel region of a CCD.

FIG. 8D illustrates the circuit configuration of the amplifier 53d that clips a signal of an idle region. The input terminal of the input circuit portion 53e described above with reference to FIG. 8B is further grounded via a series circuit including a resistance R11 and a switch SW1. That is, in the circuit configuration in FIG. 8D, at the input terminal, the resistance R11 and the switch SW1 are provided in parallel with the resistance R3.

The switch SW1 is turned on/off by a switching signal that is synchronized with the above described intermittent driving. Specifically, in a drive period the switch SW1 is turned on by the switching signal (that becomes H level), and in an idle period the switch SW1 is turned off. The input terminal is grounded with a resistance of approximately 910Ω in a drive period, and is grounded with a resistance (specifically, the resistance R3) of 10 kΩ in an idle period. Consequently, DC level of the CCD output signal Vout fluctuates between a drive period and an idle period as shown in FIG. 8C.

A signal that passes through the input circuit portion 53e that is described above is applied to the base of a transistor Q2 included in the amplifier 53d. The collector of the transistor Q2 is connected to a predetermined power supply terminal (+5V) and is also grounded via a capacitor C5. The emitter of the transistor Q2 is grounded via a resistance R12 and is also connected to the emitter of a transistor Q3 via a resistance R13.

The emitter of the transistor Q3 is grounded via a resistance 21. The collector of the transistor Q3 is connected to a predetermined power supply terminal via a resistance R14 and is also connected to the base of a transistor Q4 via a resistance R15.

The base of the transistor Q3 is grounded via a resistance R16 and a resistance R17. A connecting point between the resistances R16 and R17 is grounded via a capacitor C6 and is also connected to a predetermined power supply terminal via a resistance R18.

The collector of the transistor Q4 is connected to a predetermined power supply terminal and is also grounded via a capacitor C7. The emitter of the transistor Q4 is grounded via a resistance R19 and is also connected to the output terminal of the amplifier 53d via a series circuit including a resistance R20 and a capacitor C8. A connecting point between the resistance R20 and the capacitor C8 is grounded via a capacitor C9. Note that, the other end of the resistance R14 that has one end connected to the transistor Q3 is grounded via a capacitor C10.

The operations of the circuit configuration shown in FIG. 8D are described hereunder. The CCD output signal Vout that passes through the input circuit portion 53e and is inputted to the amplifier 53d is transmitted to the base-grounded transistor Q3 by the emitter-follower transistor Q2. A signal that has been amplified by the transistor Q3 is converted to a low impedance and outputted by the emitter-follower transistor Q4 from the collector thereof.

In this case, as shown in FIG. 8C, when signals of an idle region were amplified by the transistor Q3, a voltage at the collector of the transistor Q3 (all signals of the idle region) are equal to or greater than, for example, a clip level of 4.8 V, and accordingly all signals of the idle region are clipped at the clip level.

In contrast, for signals of an effective pixel region that were amplified by the transistor Q3, all voltages at the collector of the transistor Q3 are equal to or less than the clip level, and therefore, in practice, only signals of the effective pixel region are amplified and outputted.

To cause operations to be performed in this manner, a configuration is adopted in which a DC bias when constituting the amplifier 53d is set so as to offset to the positive level side, which enables sufficient amplification with respect to a signal of an effective pixel region, and on the other hand enables reliable clipping of a signal of an idle region.

By adopting this configuration, by means of a simple circuit configuration, it is possible to amplify only signals of an effective pixel region in the CCD 16 and output the amplified signals to the subsequent stage side of the amplifier 53d.

Further, in the present embodiment a structure is adopted in which a non-connected connector contact pin is arranged, for example, between connector contact pins of the MC 31 in which there is a large electric field intensity between the relevant connector contact pins, to thereby decrease the electric field intensity to an intensity that is about one half of the electric field intensity before arrangement of the non-connected connector contact pin therebetween.

Figure 9:
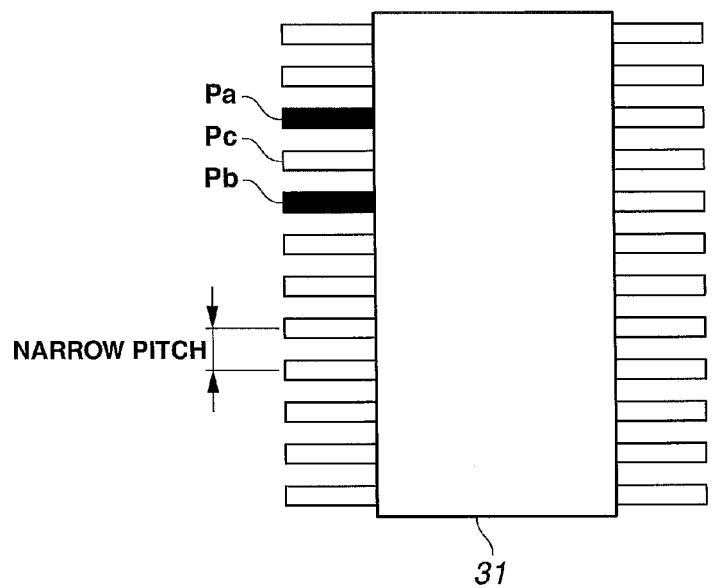
FIG. 9 is a view that illustrates a micro-connector in which a non-connected connector contact pin is provided between specific connector contact pins.

In a case where connector contact pins Pa and Pb that are adjacent to each other in the MC 31 shown in FIG. 9 are allocated to a specific signal or power supply, because a pitch between the respective connector contact pins in the MC 31 is narrow, an electric field intensity of the specific signal or power supply increases between the adjacent connector contact pins Pa and Pb and the possibility of a short circuit occurring increases. Alternatively, at a moment at which a voltage level has become large, there is a possibility that the insulation between adjacent connector contact pins will be inadequate.

Therefore, in the present embodiment, with respect to the adjacent connector contact pins Pa and Pb at which the electric field intensity exceeds a specific value, a structure is adopted in which a non-connected connector contact pin Pc (that is not connected to anything) is arranged between the two connector contact pins Pa and Pb, to thereby prevent occurrence of a short circuit or other abnormal state.

Note that a configuration may also be adopted in which the non-connected connector contact pin Pc is arranged between connector contact pins that have a large voltage difference therebetween or between connector contact pins that have a large current difference therebetween, and the configuration is not limited to a case where there is a large electric field intensity between connector contact pins.

The application example shown in FIG. 9 is not limited to the MC 31, and can also be applied to the other MC 35 or the MC receptacles 33 and 36.

In addition, in the present embodiment, a sensor is mounted that prevents deterioration in the characteristics of electronic components inside the endoscope 2A or corrosion of the electronic components due to humidity. Each time that the endoscope 2A is used for endoscopy, the endoscope 2A is disinfected with a chemical solution or in a state of a high temperature and high humidity atmosphere and is cleaned with a cleaning apparatus.

Consequently, when the endoscope 2A is used over a long period of time, it is possible that moisture may enter inside the endoscope 2A. If the endoscope 2A is used by passing a current thereto in a state in which the interior thereof has a humidity that is equal to or greater than a predetermined humidity, deterioration or corrosion of electronic components or substrates inside the endoscope 2A is accelerated in comparison to the case of a normal usage state.

Therefore, a humidity sensor 71 for detecting the humidity inside the endoscope 2A is provided on (for example, the A/D substrate 24B of) the connector substrate 24 as shown by a dashed line in FIG. 1, and a humidity detection circuit 72 that detects (calculates) the humidity inside the endoscope 2A by means of a detection signal of the humidity sensor 71 is provided inside the processor 4.

When the detected humidity is a high humidity that is equal to or greater than a predetermined threshold value, the humidity detection circuit 72 outputs a warning signal to the control circuit 29 to warn the control circuit 29 to the effect that the current state is a high humidity state in which the detected humidity is equal to or greater than the predetermined threshold value. When the warning signal is inputted thereto, the control circuit 29 performs control with respect to the power supply circuit 27 to stop the supply of power to the endoscope 2A side and also outputs the warning signal to the signal processing circuit 28.

The signal processing circuit 28 performs signal processing so as to display a warning message corresponding to the warning signal on the monitor 5. In this case, as described hereunder, on the endoscope 2A side, a configuration is adopted so that, in a state in which power is not supplied, the humidity detection circuit 72 drives the humidity sensor 71 and judges the humidity state by means of a detection signal that is outputted from the humidity sensor 71, and can display a warning message on the monitor 5 if the humidity is a high level.

A member that enables construction of the humidity sensor 71 using a passive component that allows the humidity inside the endoscope 2A to be detected by the humidity sensor 71 without supplying power to the endoscope 2A side is further preferable.

As a member that corresponds thereto, a resistance-type humidity sensor that detects a change in humidity as a change in an impedance of a moisture sensitive membrane or a capacitive humidity sensor that detects a change in humidity as a change in an electrostatic capacity between a pair of electrodes can be used.

In the endoscope apparatus 1 of the present embodiment, when the humidity sensor 71 is provided inside the endoscope 2A as described above and it is detected that the inside of the endoscope 2A is a high humidity state that is higher than a normal humidity state, in a state in which the supply of power to the endoscope 2A side is stopped and deterioration or the occurrence of a failure of an electronic component due to passage of a current thereto in a high humidity state is effectively prevented, a warning (notification) to the effect that the state is a high humidity state is notified to the user. By notifying the user of such fact, the user can swiftly perform repairs to eliminate the high humidity state.

In addition, a configuration may also be adopted that, without using the above described humidity sensor 71, uses a dummy component that is described below that has a characteristic such that the properties thereof are liable to be deteriorated by humidity in comparison to electronic components that are actually used inside the endoscope 2A as described hereunder.

Figure 10A:
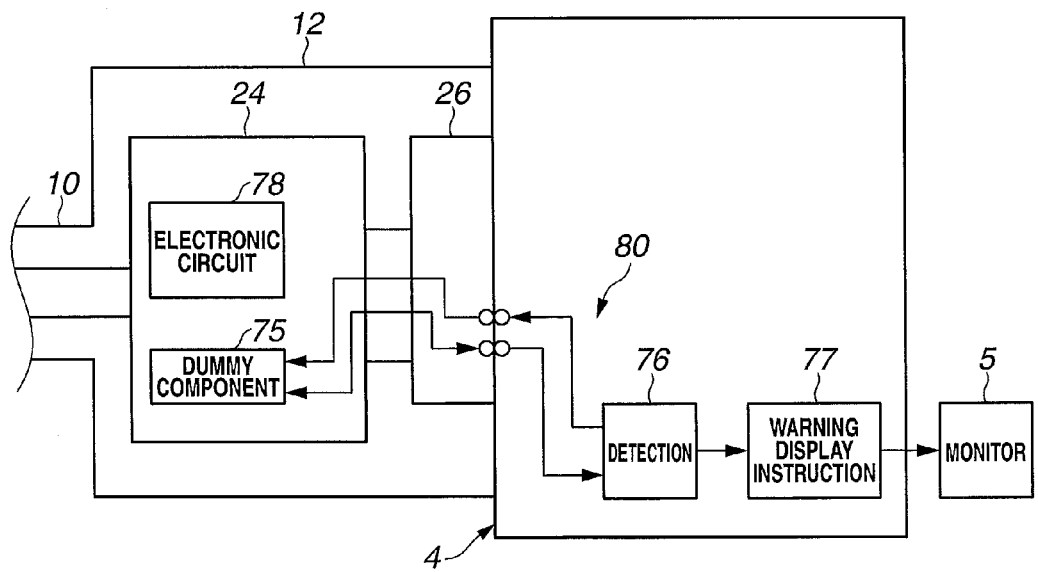
FIG. 10A is a view that illustrates the configuration of a corrosion abnormality detection apparatus that detects the occurrence of corrosion using a dummy component.

FIG. 10A shows a configuration in a case where, instead of the humidity sensor 71 shown in FIG. 1, a dummy component 75 having the above described characteristic is provided to detect corrosion. The dummy component 75 is mounted on (for example, the A/D substrate 24B of) the connector substrate 24 inside the signal connector 12 in the endoscope 2A. An electrical characteristic of the dummy component 75 is detected by a detection circuit 76 inside the processor 4. The detection circuit 76 compares the detection result with a threshold value and judges whether or not an abnormal state exists that is caused by corrosion. Note that although FIG. 10A illustrates a case in which the dummy component 75 is provided on the single connector substrate 24, a configuration may also be adopted in which the dummy component 75 is provided on a plurality of substrates inside the endoscope 2A.

If the detection circuit 76 judges that there is an abnormal state, the detection circuit 76 outputs a judgment signal to that effect to a warning display instruction circuit 77. The warning display instruction circuit 77 outputs a warning message to the effect that the detection circuit 76 detected an abnormal state to the monitor 5 to notify the user that there is an abnormal state caused by corrosion.

A corrosion abnormality detection apparatus 80 that detects the occurrence of an abnormal state due to corrosion is constituted by the dummy component 75, the detection circuit 76 and the warning display instruction circuit 77.

Note that reference numeral 78 in FIG. 10A denotes an electronic circuit that is formed by the FPGA 51 and the like.

The following requirements can be conceivable with respect to shape and characteristics in the case of providing the above described dummy component 75. As causes of a deterioration in characteristics due to moisture or the like or a failure due to corrosion of a print pattern of a substrate, for example, when elution of a solder or an element plating portion is assumed, it is conceivable that a short-circuit state is reached between terminals or between exposure patterns due to the eluted metal, or a failure may arise whereby a terminal or a pattern gets thinner and reaches an open circuit state.

Therefore, a shape requirement of the dummy component 75 is to have a pattern in which a pitch between terminals is narrower than a component that is used in the product, and a characteristic requirement of the dummy component 75 is that the dummy component 75 is a device with which it is possible to distinguish between a short circuit and an open circuit.

For example, if the smallest pitch (between terminals) that is used in a product of the connector substrate 24 is 0.5 mm, a resistor having a predetermined resistance value R of several kΩ of 0402 size (0.4 mm×0.2 mm) is mounted in the connector substrate 24 and taken as the dummy component 75.

The resistance value of the above described resistor is monitored by the detection circuit 76, and if the monitored resistance value becomes equal to or greater than a threshold value Rt1 (=R+Δ) that is larger than the predetermined resistance value R by an amount Δ or if the monitored resistance value becomes equal to or less than a threshold value Rt2 (=R−4) that is smaller than the predetermined resistance value by the amount Δ, the detection circuit 76 judges that there is an abnormal state in which corrosion has occurred. The abnormal state judgment result is then notified to the user by means of the monitor 5.

Figure 10B:
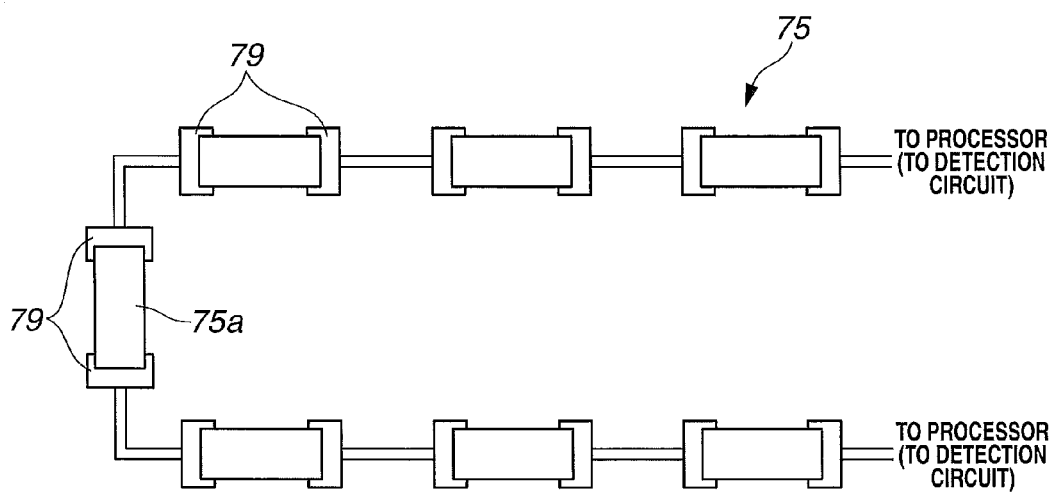
FIG. 10B is a view that illustrates the configuration of a dummy component that is a modification of the configuration shown in FIG. 10A.

In the above description, an example is described in which one resistor is mounted between narrow terminals to form the dummy component 75. However, as shown in FIG. 10B, a configuration may also be adopted in which the dummy component 75 is formed by mounting respective resistors 75a between pads 79 as a plurality of narrow terminals provided on a serial pattern. The function that detects corrosion may also be enhanced by mounting the plurality (seven resistors in FIG. 10B) of resistors 75a so as to form a series connection between the plurality of narrow terminals provided in a wide area in which corrosion may occur in this manner.

By mounting the dummy component 75 in which a fault is liable to occur due to corrosion inside the endoscope 2A, it is possible to prevent or reduce the occurrence of a situation in which the endoscope 2A is used in an abnormal state by promptly detecting an abnormal state in which a fault is liable to occur, and notifying the user to prompt the user to perform repairs.

According to the present embodiment that has been described with reference to FIG. 4A and the like, an endoscope can be provided that, even in a case where an image pickup device is driven with a plurality of power supply voltages using small-size connectors, facilitates prompt detection of an abnormal state of a power supply voltage caused by a short circuit or the like and prompt elimination of the abnormal state.

Note that although the case of the endoscope 2A has been mainly described as the aforementioned endoscope, it is clear that the description can be similarly applied to the endoscopes 2B and 2C that have a configuration relating to the described portions.

Further, in FIG. 4A to FIG. 4C, a configuration is illustrated that compares a digital voltage that has been obtained by A/D conversion by A/D conversion means with a threshold value at the comparison circuit 64 as voltage comparing means. However, a configuration may also be adopted in which the A/D conversion means is not provided, and which uses analog voltage comparing means that compares an analog voltage with a threshold value.

Note that although in FIG. 4A to FIG. 4C a configuration is illustrated that includes the CCD power supply circuit 53b' as power supply generation means that, based on a plurality of power supply voltages that are supplied from the processor 4 side, further generates a different plurality of power supply voltages inside the endoscope 2A and supplies the different plurality of power supply voltages to the CCD 16, the present invention is not limited to that configuration. For example, the present invention can also be applied in the case of a configuration in which the CCD power supply circuit 53b' is not provided, and that directly supplies the plurality of power supply voltages generated at the processor 4 to the CCD 16 via power supply wires such as the power supply wires 60a and 60b.

Figure 11:
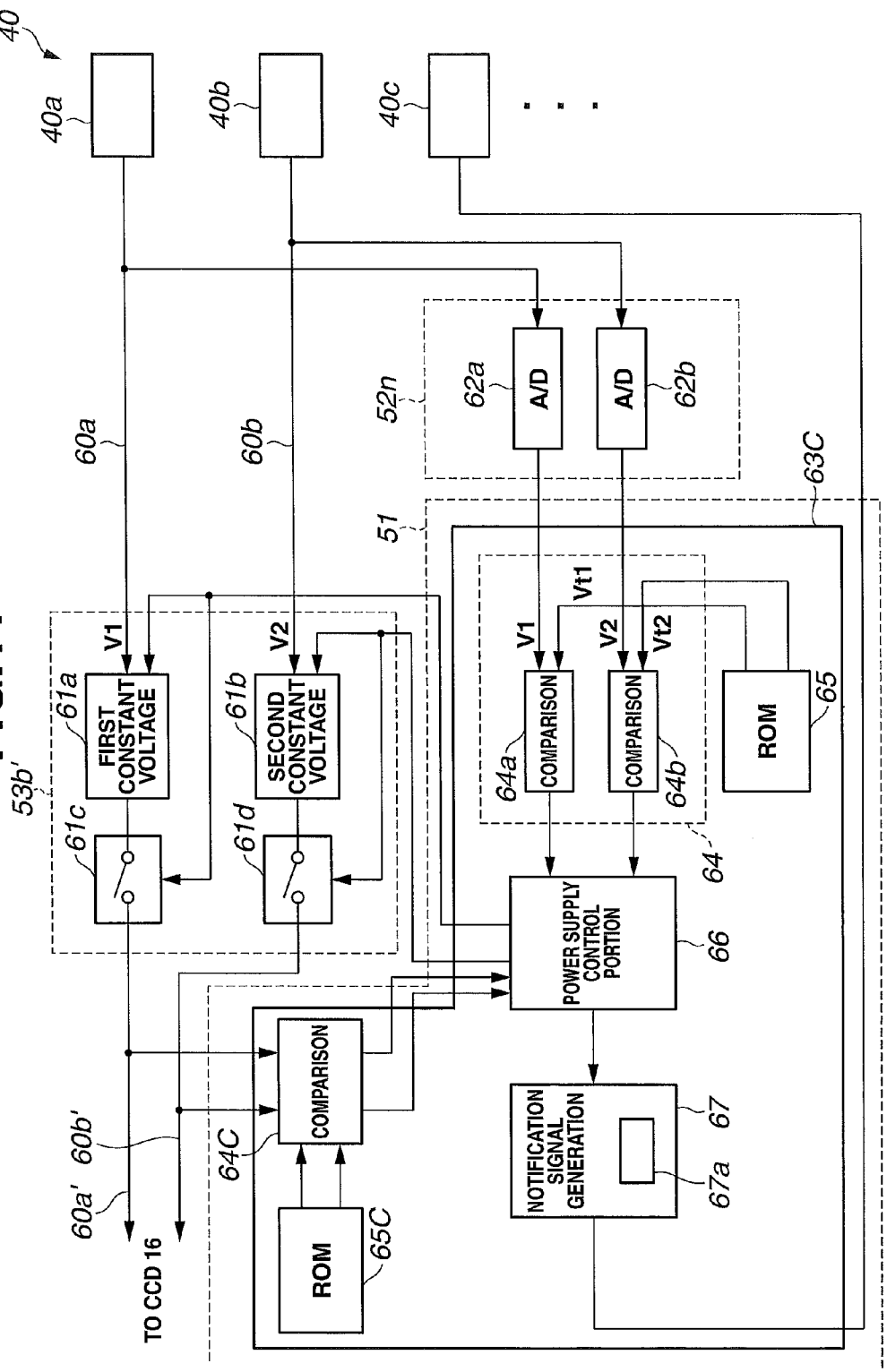
FIG. 11 is a view that illustrates the configuration of a CCD power supply voltage monitoring circuit that is a modification of the configuration shown in FIG. 4A.

In addition, in the case of a configuration in which the CCD power supply circuit 53b' is included inside the endoscope 2A as shown in FIG. 4A to FIG. 4C, a configuration may also be adopted that further monitors the power supply voltages of the plurality of power supplies that are outputted from the CCD power supply circuit 53b' and controls the supply of power to the CCD 16 in accordance with the monitoring result, and for example, a configuration that is shown in FIG. 11 may be adopted. Note that the present configuration may be applied to the in-substrate circuit power supply circuit 52p shown in FIG. 3 so as to control the supply of power to circuits in the substrate in accordance with the monitoring result of the power supply voltages of the in-substrate circuit power supply circuit 52p.

A CCD power supply voltage monitoring circuit 63C shown in FIG. 11 has a configuration that, relative to the configuration of the CCD power supply voltage monitoring circuit 63 shown in FIG. 4A, further includes a comparison circuit 64C and a ROM 65C. In this case, a configuration is adopted in which two power supply voltages that are outputted to the CCD 16 via the switches 61c and 61d of the CCD power supply circuit 53b' are respectively compared with a threshold value from the ROM 65C by the comparison circuit 64C (that contains two comparison circuits therein similarly to the comparison circuit 64) as second voltage comparing means, and the comparison results are outputted to the power supply control portion 66.

The power supply control portion 66 monitors the plurality of power supply voltages on the input terminal side and output terminal side of the CCD power supply circuit 53b', and allows the CCD power supply circuit 53b' to operate as it is if the judgment result is that the voltages are in a normal voltage range. On the other hand, in the case of a judgment result to the effect that there is an abnormal voltage that is outside the normal voltage range, the power supply control portion 66 controls so as to cut off the power supply voltage that is supplied to the CCD 16 side from the CCD power supply circuit 53b'. Further, in the case of a judgment result to the effect that there is an abnormal voltage, the power supply control portion 66 controls so that notification thereof is performed by the notification signal generation circuit 67. By adopting this configuration, an abnormal state of the power supply inside an endoscope such as the endoscope 2A can be swiftly detected in a more detailed manner to enable swift performance of a countermeasure that eliminates the abnormal state.

Note that although the CCD power supply voltage monitoring circuit illustrated in the above described FIG. 4A to FIG. 4C, FIG. 11, and the like has been described in the foregoing, a configuration may also be adopted that detects a short circuit between connector contact pins that relay respectively different power supply voltages or the like, by comparing voltages between two power supplies (between two different power supplies that generate different power supply voltages) that are different from each other as described below.

Figure 12:
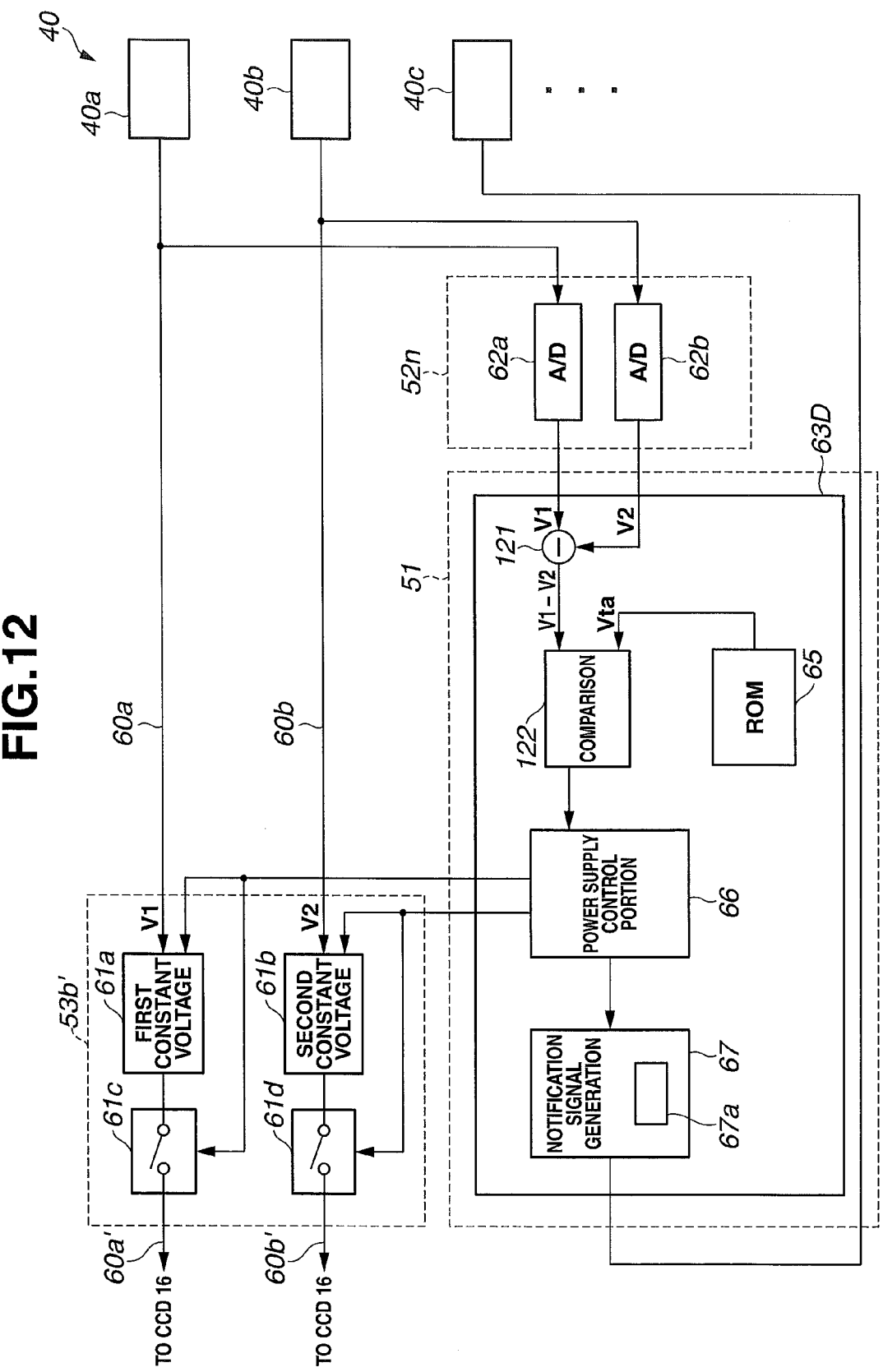
FIG. 12 is a view that illustrates the configuration of a CCD power supply voltage monitoring circuit that is a different modification of the configuration shown in FIG. 4A.

FIG. 12 illustrates a CCD power supply voltage monitoring circuit 63D that compares voltages between (power supply) voltages V1 and V2 of power supply wires 60a and 60b that are relayed by adjacent connector-receptacle contact pins 40a and 40b, to thereby detect a short circuit or an insulation failure that falls short of being a short circuit between the adjacent connector-receptacle contact pins 40a and 40b.

For example, relative to the CCD power supply voltage monitoring circuit 63 shown in FIG. 4A, instead of the comparison circuit 64 into which the digital voltages V1 and V2 that passed through the A/D conversion circuits 62a and 62b are inputted, the CCD power supply voltage monitoring circuit 63D includes a subtractor 121 as subtraction means that generates a differential voltage between the two voltages V1 and V2 and a comparison circuit 122. Note that the present configuration is not limited to a case that is applied to FIG. 4A, and may also be applied to FIG. 4B and the like.

The two voltages V1 and V2 are inputted to the comparison circuit 122 as comparison means via the subtractor 121 that generates a differential voltage between the two voltages V1 and V2 by subtracting the smaller voltage from the larger voltage. Here, the larger voltage is described as V1 (that is, V1>V2). The comparison circuit 122 compares the (voltage generated by the subtractor 121 as the) differential voltage V1−V2 between the two voltages V1 and V2 and a threshold value Vta that serves as a voltage value for judging a short circuit or an insulation failure that is previously stored in the ROM 65.

The threshold value Vta will now be described. A voltage value that is inputted to the comparison circuit 122 via the subtractor 121 in a case where, for example, the connector-receptacle contact pins 40a and 40b are connected with a resistance value that corresponds to occurrence of an insulation failure is previously stored in the ROM 65 as the threshold value Vta. In other words, information of the threshold value Vta for judging the occurrence of an insulation failure that is at a stage prior to becoming a short-circuit state is stored in the ROM 65. The comparison circuit 122 compares the differential voltage V1-V2 and the threshold value Vta, and outputs the comparison result to the power supply control portion 66.

The power supply control portion 66 controls the supply of power to the CCD 16 side based on the comparison result. If the comparison result indicates that V1-V2>Vta, the power supply control portion 66 judges that the current state is a normal state in which a short circuit or an insulation failure has not occurred. If the comparison result indicates that V1-V2≤Vta, the power supply control portion 66 judges that the current state is an abnormal state in which a short circuit or an insulation failure has occurred.

In the normal state, the condition V1-V2>Vta is satisfied. At a time that an insulation failure occurs, the comparison result becomes approximately V1-V2=Vta, and as the insulation failure proceeds, a state is entered in which the comparison result is V1-V2<Vta. Further, in a case where a short circuit appears to have occurred, V1-V2<Vta enters a state that is close to 0<Vta.

In the former case in which the comparison result is V1-V2>Vta, the power supply control portion 66 causes the CCD power supply circuit 53b' to continue operation. In contrast, in the latter abnormal state in which the comparison result is V1-V2≤Vta, the power supply control portion 66 stops operation of the CCD power supply circuit 53b' and the like, and outputs an abnormality judgment signal to the notification signal generation circuit 67.

The notification signal generation circuit 67 generates a notification signal that notifies to the effect that there is an abnormal state in which a short circuit or an insulation failure has occurred between the connector-receptacle contact pins 40a and 40b, and transmits the notification signal to the processor 4 side using the notification signal superimposing circuit 67a.

The control circuit 29 of the processor 4 outputs the notification signal to the signal processing circuit 28. The signal processing circuit 28 superimposes the notification signal upon a video signal. The monitor 5 displays the notification signal together with an endoscopic image. By means of the notification signal, the surgeon can quickly recognize that a short circuit or insulation failure has occurred between the connector-receptacle contact pins 40a and 40b.

Accordingly, with respect to the endoscope 2A in which an abnormal state occurred, repairs that correspond to the occurrence of the abnormal state can be quickly performed, and the abnormal state can be eliminated.

Note that although FIG. 12 illustrates a configuration that, in order to detect the occurrence of a short circuit or an insulation failure between the connector-receptacle contact pins 40a and 40b, compares a differential voltage between (power supply) voltages V1 and V2 that are transmitted by the power supply wires 60a and 60b with the threshold value Vta, a configuration may also be adopted that compares a differential voltage between power supply voltages that are transmitted by the other two power supply wires (for example, 60a' and 60b') with a corresponding threshold value to detect the occurrence of a short circuit or an insulation failure between (in particular, adjacently arranged) connector contact pins by which the other two power supply wires are relayed, respectively.

Furthermore, the subtractor 121 and the comparison circuit 122 may be additionally provided in the configurations illustrated in FIG. 4A and FIG. 4B and the like to add a function that detects the occurrence of a short circuit or an insulation failure between the connector-receptacle contact pins 40a and 40b. Further, an embodiment that is configured by partially combining the above described embodiment and the like also belongs to the present invention.

What is claimed is:

1. An endoscope, comprising:
an image pickup device that is mounted in a distal end portion of an insertion portion;
wiring that transmits a power supply having a plurality of different power supply voltages for driving the image pickup device, a drive signal that drives the image pickup device, an image pickup signal that is outputted from the image pickup device that is driven by the drive signal, and a ground level;
a substrate on which a connector that relays the wiring is provided;
a first voltage comparing portion that compares the plurality of different power supply voltages;
a power supply generation portion that, based on the plurality of different power supply voltages, generates a plurality of second power supply voltages that are respectively different from the plurality of different power supply voltages;
a second voltage comparing portion that compares the plurality of second power supply voltages; and
a power supply control portion that controls a supply of power to the image pickup device based on a comparison result of the first voltage comparing portion and a comparison result of the second voltage comparing portion, wherein
the first voltage comparing portion is provided on the substrate, and the first voltage comparing portion outputs a comparison result regarding whether or not each power supply voltage is within a normal voltage range by comparing the plurality of power supply voltages and respective predetermined threshold values, and
the power supply control portion is provided on the substrate, and the power supply control portion controls so as to supply power to the image pickup device in a case where the comparison result of the first voltage comparing portion is within the normal voltage range, and controls so as to stop supply of power to the image pickup device in a case where the comparison result of the first voltage comparing portion is outside the normal voltage range.

2. The endoscope according to claim 1, wherein:
the power supply control portion comprises a notification signal transmission portion that, in a case where the comparison result of the first voltage comparing portion indicates an abnormal voltage that is outside the normal voltage range, transmits a notification signal that notifies occurrence of the abnormal voltage to a signal processing apparatus that performs signal processing with respect to the image pickup device, to which the endoscope is detachably connected.

3. The endoscope according to claim 2, wherein:
in a case where the comparison result of the first voltage comparing portion indicates an abnormal voltage that is outside the normal voltage range, the first voltage comparing portion stops operation of the power supply generation portion into which the abnormal voltage is inputted.

4. The endoscope according to claim 3, wherein:
the first voltage comparing portion and the power supply control portion are configured using an FPGA that is programmably constructed.

5. The endoscope according to claim 4, wherein:
the power supply control portion comprises a notification signal superimposing portion that superimposes the notification signal upon another signal that is other than the notification signal and transmits the resulting signal to the signal processing apparatus to which the endoscope is detachably connected.

6. An endoscope comprising:
an image pickup device that is mounted in a distal end portion of an insertion portion;
wiring that transmits a power supply having a plurality of different power supply voltages for driving the image pickup device, a drive signal that drives the image pickup device, an image pickup signal that is outputted from the image pickup device that is driven by the drive signal, and a ground level;
a substrate on which a connector that relays the wiring is provided;
a first voltage comparing portion that compares the plurality of different power supply voltages;
a power supply generation portion that, based on the plurality of different power supply voltages generates a plurality of second power supply voltages that are respectively different from the plurality of different power supply voltages;
a second voltage comparing portion that compares the plurality of second power supply voltages;
a power supply control portion that controls a supply of power to the image pickup device based on a comparison result of the first voltage comparing portion and a comparison result of the second voltage comparing portion;
a subtraction circuit that generates a differential voltage between two power supply voltages that are different from each other in the power supply having the plurality of different power supply voltages that are respectively relayed by two connector contact pins that are adjacent in the connector; and
a comparison circuit that compares the differential voltage that is generated by the subtraction circuit and a threshold value that is set for detecting a short circuit or an insulation failure between the two connector contact pins;
wherein the power supply control portion controls the supply of power to the image pickup device based on a comparison result obtained by the comparison circuit.

7. The endoscope according to claim 2, further comprising:
a subtraction circuit that generates a differential voltage between two power supply voltages that are different from each other in the power supply having the plurality of different power supply voltages that are respectively relayed by two connector contact pins that are adjacent in the connector; and
a comparison circuit that compares the differential voltage that is generated by the subtraction circuit and a threshold value that is set for detecting a short circuit or an insulation failure between the two connector contact pins;
wherein the power supply control portion controls the supply of power to the image pickup device based on a comparison result obtained by the comparison circuit.

8. The endoscope according to claim 5, further comprising:
a subtraction circuit that generates a differential voltage between two power supply voltages that are different from each other in the power supply having the plurality of different power supply voltages that are respectively relayed by two connector contact pins that are adjacent in the connector; and
a comparison circuit that compares the differential voltage that is generated by the subtraction circuit and a threshold value that is set for detecting a short circuit or an insulation failure between the two connector contact pins;
wherein the power supply control portion controls the supply of power to the image pickup device based on a comparison result obtained by the comparison circuit.

9. The endoscope according to claim 3, wherein:
the substrate comprises an excessive current detection circuit that detects whether or not a power supply current of the power supply that is supplied to the power supply generation portion from a power supply circuit that is provided in an external apparatus to which the endoscope is detachably connected is an excessive current that is equal to or greater than a predetermined value, and if the excessive current detection circuit detects an excessive current, the excessive current detection circuit cuts off a power supply current in which the excessive current is detected.

10. The endoscope according to claim 6, wherein:
the substrate comprises an excessive current detection circuit that detects whether or not a power supply current of the power supply that is supplied to the power supply generation portion from a power supply circuit that is provided in an external apparatus to which the endoscope is detachably connected is an excessive current that is equal to or greater than a predetermined value, and if the excessive current detection circuit detects an excessive current, the excessive current detection circuit cuts off a power supply current in which the excessive current is detected.

11. The endoscope according to claim 3, wherein:
the substrate comprises a power supply on/off control circuit that, in a case where the power supply that is supplied to the power supply generation portion from a power supply circuit that is provided in an external apparatus to which the endoscope is detachably connected is turned on and off, cuts off the plurality of second power supply voltages that the power supply generation portion generates after a short time period of t1 from a timing at which the power supply is turned off, and after a time period t2 that is greater than the time period t1 from a timing at which the power supply is turned on, turns on the power supply generation portion so as to output the plurality of second power supply voltages that the power supply generation portion generates.

12. The endoscope according to claim 2, wherein:
the substrate comprises a connector substrate that is provided inside a connector at which the endoscope is detachably connected to the signal processing apparatus, and a distal end portion substrate that is provided in the distal end portion of the insertion portion of the endoscope and to which the image pickup device is connected; and
the wiring detachably connects the connector substrate and the distal end portion substrate.

13. The endoscope according to claim 7, wherein:
the substrate comprises a connector substrate that is provided inside a connector at which the endoscope is detachably connected to the signal processing apparatus, and a distal end portion substrate that is provided in the distal end portion of the insertion portion of the endoscope and to which the image pickup device is connected; and the wiring detachably connects the connector substrate and the distal end portion substrate.

14. The endoscope according to claim 13, wherein:

the substrate further comprises an operation portion substrate that is arranged in an operation portion that is provided at a proximal end of the insertion portion in the endoscope; and the wiring comprises a first cable that detachably connects the connector substrate and the operation portion substrate, and a second cable that detachably connects the operation portion substrate and the distal end portion substrate.

* * * * *